US007521057B2

(12) United States Patent
Sower et al.

(10) Patent No.: US 7,521,057 B2
(45) Date of Patent: Apr. 21, 2009

(54) LAMPREY GNRH-III POLYPEPTIDES AND METHODS OF MAKING THEREOF

(75) Inventors: Stacia Sower, Newmarket, NH (US); Matthew Silver, Dover, NH (US)

(73) Assignee: University of New Hampshire, Durham, NH (US)

( * ) Notice: Subject to any disclaimer, the term of this patent is extended or adjusted under 35 U.S.C. 154(b) by 44 days.

(21) Appl. No.: 11/172,274

(22) Filed: Jun. 30, 2005

(65) Prior Publication Data

US 2006/0014253 A1 Jan. 19, 2006

Related U.S. Application Data

(62) Division of application No. 10/170,096, filed on Jun. 12, 2002, now Pat. No. 6,949,365.

(51) Int. Cl.
*A61K 39/00* (2006.01)
(52) U.S. Cl. ............... 424/198.1; 530/300; 530/313; 530/333; 424/192.1
(58) Field of Classification Search ............... None
See application file for complete search history.

(56) References Cited

U.S. PATENT DOCUMENTS

| | | | |
|---|---|---|---|
| 4,410,514 A | 10/1983 | Vale, Jr. et al. | |
| 5,076,208 A | 12/1991 | Zohar et al. | |
| 5,093,246 A | 3/1992 | Cech et al. | |
| 5,643,877 A | 7/1997 | Zohar et al. | |
| 6,210,927 B1 | 4/2001 | Zohar et al. | |
| 6,664,369 B1 * | 12/2003 | Lovas et al. | 530/328 |

FOREIGN PATENT DOCUMENTS

WO    WO 96/04927    *   2/1996

OTHER PUBLICATIONS

Sequence alignment between SEQ ID No. 8 of the present application and locus Q918X8_PETMA. Accessed Sep. 10, 2007.*
Sequence alignment between amino acids 1-10 of SEQ ID No. 8 of the present application and locus GON3_PETMA. Accessed Sep. 10, 2007.*
Locus AF144480 and Q918X8, Suzuki et al., J. Mol. Endocrinol., 2000, 24:365-376 (sequence search results only).*
Adelman, J.P., Mason, A.J. Hayflick, J.S., and Seeburg, P.H., "Isolation of the gene and hypothalamic . . . " Proc. Natl. Acad. Sci. USA, 1st ed., p. 179-183, (Jan. 11, 1986).
Alestrom, P., Kisen, G., Klungland, H., and Andersen, O., "Fish gonadotropin-releasing hormone gene . . . " Molecular Marine Biology and Biotechnology, p. 376-379, (Jun. 11, 1992).
Ashihara, M., Suzuki, M., Kubokawa, K., Yoshiura, Y., Kobayashi, M., Urano, A., and Aida, K., "Two differing precursor genes for the salmon-type gonadotropin-releasing hormone exist in salmonids," J Mol Endocrinol, p. 1-9, (Jun. 11, 1995).
Bogerd, J., Zandbergen. T., Andersson, E., Andgoos, H., "Isolation, characterization and expression of cDNAs encoding the catfish-type and chicken-II-type gonadotropin-releasing-hormone precursors in the African catfish." Eur J. Biochem. p. 541-9, (Jun. 11, 1994).
Bond, C.T., Francis, R.C., Fernald, R.D., and Adelman, J.P., "Characterization of Complementary DNA Encoding the Precursor for Gonadotropin-Releasing Hormone and Its Associated Peptide from a Teleost Fish," Molecular Endocrinology, p. 931-7, (Jun. 11, 1991).
Bond, C.T., Hayflick, J.S., Seeberg, P.H., and Adelman, J.P., "The Rat Gonadotropin-Releasing Hormone: SH Locus: Structure and Hypothalamic Expression," Molecular Endocrinology, p. 1257-62, (Jun. 11, 1989).
Burgus, R., Butcher, M., Amoss, M., Ling, N., Monahan, M., Rivier, J., Fellos, R., Blackwell, R., Vale, W., and Guillemin, R., "Primary Structure of the Ovine-Hypothalamic Luteinizing Hormone . . . " Proc. Nat. Acad. Science, vol. 69 (No. 1), p. 278-282, (Jan. 11, 1972).
Carolsfeld, J., Powell, J.F., Park, M., Fischer, W.H., Craig, A.G., Chang, J.P., Rivier, J.E. and Sherwood, N.M., "Primary Structure and Function of Three Gonadotropin-Releasing Hormones Including a Novel Form. from an Ancient Telcost Herring." Endocrinology, p. 505-12. (Jun. 11, 2000).
Chen, T.T., and Powers, D.A., "Transgenic fish," Trends Biotechnol, p. 209-15, (Jun. 11, 1990).
Chow. M.M., Kight, K.E., Gothilf, Y., Alok, D., Stubblefield, J., and Zohar, Y., "Multiple GnRHs present in a teleost species are encoded by separate genes: analysis of the sbGnRH and cGnRH-II genes from the striped bass, Morone saxatilis," Journal of Molecular Endocrinology, p. 277-89, (Jun. 11, 1998).
Coe, I.R., Von Schalburg, K.R., and Sherwood, N.M., "Characterization of the Pacific salmon gonadotropin-releasing hormone gene, copy number and transcription start site," Molecular and Cellular Endocrinology, Elsevier Science Ireland Ltd., p. 113-22, (Jun. 11, 1995).
Deragon, K.L., and Sower, S.A., "Effects of Lamprey Gonadotropin-Releasing Hormone-III . . . " General and Comparative Endocrinology. Academic Press. Inc. (USA). p. 363-7. (Jun. 11, 1994).
Dong, K.W., Duval, P., Zeng, Z., Gordon, K., Williams,R.F., Hodgen, G.D., Jones, G., Kerdeliiue, B., and Roberts, J.L., "Multiple transcription start sites for the GnRH gene in rhesus . . . " Molecular and Cellular Endocrinology. Elsevier Science Ireland Ltd. (USA). p. 121-30. (Jun. 11, 1996).
Dunn, I.C., Chen, Y., Hook, C., Sharp, P.J. and Sang, H.M., "Characterization of the chicken preprogonadotrophin-releasing-I gene," Journal of Molecular Endocrinology, Journal of Endocrinology Ltd (Great Britain), p. 19-29, (Jun. 11, 1993).
Gazourian, L., Deragon, K.L., Chase., C.F., Pati, D., Habibi, H.R., and Sower, S.A., "Characteristics of GnRH Binding in the Gonads and Effects of Lamprey GnRH-I . . . " General and Comparative Endocrinology, Academic Press (USA), p. 327-339, (Jun. 11, 1997).
Gothilf, Y., Elizur, A., Chow. M., Chen, T.T., and Zohar, Y., "Molecular cloning and characterization of a novel gonadotropin-releasing hormone from the gilthead seabream (Sparus aurata)," Molecular Marine Biology and Biotechnology. vol. 4 (No. 1). p. 27-35, ( Jun. 11, 1995).

(Continued)

*Primary Examiner*—Dong Jiang
(74) *Attorney, Agent, or Firm*—Devine, Millimet & Branch PA; Raymond I. Bruttomesso, Jr.; Paul A. Remus

(57) ABSTRACT

Lamprey GnRH-III polypeptides for the four species of fish lamprey are disclosed. Also disclosed is a procedure for producing such polypeptides by recombinant techniques. Also disclosed are methods for utilizing such polypeptides for sterilizing fish.

7 Claims, 5 Drawing Sheets

OTHER PUBLICATIONS

Grober, M.S., Myers, T.R., Marchaterre, M.A., Bass, A.H., and Myers, D.A., "Structure, Localization, and Molecular Phylogeny of a GnRH cDNA . . . " General and Comparative Endocrinology, Academic Press, Inc. (USA), p. 85-99, (Jun. 11, 1995).

Gubler, U., and Hoffman, B.J., "A simple and very efficient method for generating cDNA libraries," Gene, Elsevier Science Publishers (USA), p. 263-9. (Jun. 11, 1983).

Hayes, W.P., Wray, S., and Battey, J.F., "The Frog Gonadotropin-Releasing Hormone-I (GnRH-I) Gene Has a Mammalian-Like Expression Pattern and Conserved Domains in GnRH . . . " Endocrinology, The Endocrine Society (USA), vol. 134 (No. 4), p. 1835-45, (Jun. 11, 1994).

Jimenez-Linan, M., Rubin, B.S., and King, J.C., "Examination of Guinea Pig Luteinizing Hormone-Releasing Hormone Gene Reveals a Unique Decapeptide and Existence of Two Transcripts in the Brain." Endocrinology. The Endocrine Society (USA), vol. 138 (No. 10), p. 4123-30. (Jun. 11, 1997).

Kasten, T.L, White, S.A., Norton, T.T., Bond, C.T., Adelman, J.P. and Fernald, R.D., "Characterization of Two New preproGnRH mRNAs in the Tree Shrew: First Direct Evidence for Mesencephalic GnRH Gene Expression in a Placental Mammal," General and Comparative Endocrinology, Academic Press, Inc. (USA), p. 7-19, (Jun. 11, 1996).

King, J.A., and Millar, R.P., "Structure of Chicken Hypothalamic Luteinizing Hormone-releasing Hormone . . . " The Journal of Biological Chemistry, vol. 257 (No. 18), p. 10722-1072, (Jun. 11, 1982).

King, J.A., and Millar, R.P., "Structure of Chicken Hypothalamic Luteinizing Hormone-releasing Hormone II . . . " The Journal of Biological Chemistry, p. 10729-32, (Jun. 11, 1982).

King, J.C., Sower, S.A., and Anthony, E.L., "Neuronal systems immunoreactive with antiserum to lamprey gonadotropin-releasing hormone in the brain of Petromyzon marinus," Cell and Tissue Research, p. 1-8, (Jun. 11, 1988).

Klungland, H., Andersen, O., Kisen, G., Alestrom, P., and Tora, L., "The Atlantic salmon prepro-gonadotropin releasing hormone gene and mRNA," Molecular and Cellular Endocrinology. Elsevier Scientific Publishers Ireland. Ltd. (USA), p. 420-25, (Jun. 11, 1992).

Klungland. H., Lorens. J.B., Andersen. O., Kisen. G.O., and Alestrom, P., "The salmon gonadotropin-releasing hormone encoding gene in salmonids," Molecular Marine Biology and Biotechnology, Blackwell Scientific Publications, Inc. (USA), p. 167-74, (Jun. 11, 1992).

Lin, X.W., and Peter, R.E., "Expression of Salmon Gonadotropin-Releasing Hormone (GnRH) and Chicken GnRH-II Precursor Messenger Ribonucleic Acids in the Brain and Ovary of Goldfish," General and Comparative Endocrinology. Academic Press. Inc. (USA), p. 282-296, (Jun. 11, 1996).

Lovejoy, D.A., Fischer, W.H., Ngamvongchon, S., Craig, A.G., Nahorniak, C.S., Peter, R.E., Rivier, J.E., and Sherwood, N.M., "Distinct sequence of gonadotropin-releasing hormone (GnRH) in dogfish brain . . . " Proc. National Academy of Science, p. 6373-6377, (Jul. 11, 1992).

Macintyre, J.K., Chase, C., Tobet, S.A., and Sower, S.A., "The interrelationship of PMY, GABA and GnRH in the sea lamprey, Petromyzon marinus," XIII International Congress of Comparative Endocrinology, p. 721-724, (Jun. 11, 1997).

Mason, A.J., Hayflick, J.S., Zoeller, R.T., Young, W.S., 3RD, Phillips, H.S., Nikolics, K., and Seeburg, P.H., "A Deletion Truncating the Gonadotropin-Releasing Hormone Gene is Responsible for Hypogonadism in the hpg Mouse." Science, p. 1366-71, (Jun. 11, 1986).

Matsuo, H., Baba, Y.. Nair, R.M., Arimura, A., and Schally, A.V., "Structure of the Porcine LH and FSH-Releasing Hormone. I. The Proposed Amino Acid Sequence," Biochemical and Biophysical Research Communications, vol. 43 (No. 6), p. 1334-9, (Jun. 11, 1971).

Miyamoto, K., Hassegawa, Y., Nomura, M., Igarashi, M., Kangawa, K., and Matsuo, H., "Identification of the second gonadotropin-releasing hormone in chicken hypothalamus: Evidence that gonadotropin secretion is probalby controlled by two distinct gonadotropin-releasing hormones in avian species," Proc. national Academy of Science, p. 3874-3878, (Jun. 11, 1984).

Ngamvongchon, S., Lovejoy, D.A., Fischer, W.H., Craig, A.G., Nahorniak, C.S., Peter, R.E., Rivier, J.E., and Sherwood, N.M., "Primary Structures of Two Forms of Gonadotropin-Releasing Hormone, One Distinct and One Conserved, from Catfish Brain," Molecular and Cellular Neurosciences, Academic Press, Inc. (USA), p. 17-22, (Jun. 11, 1992).

Nozaki. M., Gorbman, A., and Sower, S.A., "The Distribution of Lamprey GnRH-III in Brains . . . " General and Comparative Endocrinology, Academic Press (USA), p. 57-67, (Jun. 11, 2000).

Okubo, K., and Aida, K., "Gonadotropin-Releasing Hormones (GnRHs) in a Primitive Teleost, the Arowana . . . " General and Comprative Endocrinology, Academic Press, Inc. (USA), p. 125-133, (Jun. 11, 2001).

Okubo, K., Amano, M., Yoshiura, Y., Suetake, H., and Aida, K., "A Novel Form of Gonadotropin-Releasing Hormone in the Medaka, Oryzias latipes," Biochemical and Biophysical Research Communications, Academic Press (USA), p. 298-303, (Jun. 11, 2000).

Okubo, K., Suetake, H., and Aida, K., "Expression of Two Gonadotropin-Releasing Hormone (GnRH) Precursor Genes in Various Tissues of the Japanese Eel and Evolution of GnRH," Zoological Science, Zoological Society of Japan (Japan), p. 471-478, (Jun. 11, 1999).

Okuzawa, K., Araki, K., Tanaka, H., and Hirose, K., "Molecular Cloning of a cDNA Encoding the Prepro-Salmon Gonadotropin-Releasing Hormone of the Red Seabream," General and Comparative Endocrinology, Academic Press, Inc. (USA), p. 234-242, (Jun. 11, 1994).

Powell, J.F., Reska-Skinner, S.M., Prakash, M.O., Fischer, W.H., Park, M., Rivier, J.E., Craig, A.G., Mackie, G.O., and Sherwood, N.M., "Two new forms of gonadotropin-releasing hormone . . . " Proc. National Academy of Science, p. 10461-64, (Sep. 11, 1996).

Powell, J.F., Zohar, Y., Elizur, A., Park, M., Fischer, W.H., Craig, A.G., Rivier, J.E., Lovejoy. D.A., and Sherwood, N.M., "Three forms of gonadotropin-releasing hormone characterized from brains of one species." Proc. National Academy of Science. p. 12081-85. (Dec. 11, 1994).

Seaburg, P.H., and Adelman, J.P., "Characterization of cDNA for precursor of human luteinizing hormone releasing hormone," Nature, p. 666-8, (Jun. 11, 1984).

Sherwood, N., Eiden, L., Brownstein, M., Spiess, J., Rivier, J., and Vale, W., "Characterization of a teleost gonadotropin-releasing hormone," National Academy of Science, p. 2794-8, (May 11, 1983).

Sherwood, N.M., Sower, S.A., Marhsak, D.R., Fraser, B.A., and Brownstein, M.J., "Primary Structure of Gonadotropin-releasing Hormone from Lamprey Brain," The Journal of Biological Chemistry, vol. 261 (No. 11), p. 4812-19, (Jun. 11, 1986).

Silver, M.R., Lee, K.J., Nozaki, M., Takahashi, A., Kawauchi, H., Joss, J., and Sower, S.A., "Molecular phylogenetic analysis within the petromyzontiforme lineage using the cDNA for lamprey gonadotropin releasing hormone-III," American Zoologist, vol. 41 (No. 6), p. 1587, (Dec. 11, 2001).

Sower, S.A., "Effects of lamprey gonadotropin-releasing hormone and analogs on steroidogeneis . . . " Fish Physiology and Biochemistry. Kugler Publications (USA). vol. 7 (No. 1-4). p. 101-107. (Jun. 11, 1989).

Sower, S.A., "Neuroendocrine control of reproduction in lampreys," Fish Physiology and Biochemistry, Kugler Publications (USA), vol. 8 (No. 5), p. 365-374, (Jun. 11, 1990).

Sower, S.A., "Brain and Pituitary Hormones of Lampreys, Recent Findings and their Evolutionary Significance," American Zoological, p. 15-38, (Jun. 11, 1998).

Sower, S.A., Chiang, Y.C., Lovas, S., and Conlon, J.M., "Primary Structure and Biological Activity of a Third Gonadotropin-Releasing Hormone from Lamprey Brain." Endocrinology. 1st ed., The Endocrine Society (USA). vol. 132 (No. 3). p. 1125-31. (Jun. 11, 1993).

Sower, S.A., "Biological Action of Lamprey Gonadotropin-Releasing Hormone in Lampreys," Proceedings of the Third International Symposium on Reproduction and Physiology of Fish, p. 40-41, (Aug. 11, 1987).

Sower, S.A., Dickhoff, W.W., Gorbman, A., Vale, W.W., and Rivier, J.E., "Ovulatory and steroidal responses int he lamprey following administration of salmon gonadotropin and agonistic and antagonistic analogues of gonadotropin-releasing hormone," Can. J. Zool., p. 2653-59, (Jun. 11, 1983).

Sower, S.A., and Hanson, L.H., "Vertebrate Sex Determination/Differentiation Workshop," Great Lakes Fishery Commission Publication, p. 1-55, (Jun. 11, 1992).

Suzuki, M., Gamble, R.L., and Sower, S.A., "Multiple Transcripts Encoding Lamprey Gonadotropin-Releasing Hrmone-I Precursors," Journal of Molecular Endocrinology. p. 365-376, (Jun. 11, 2000).

Suzuki, M., Iiyodo, S., Kobayashi, M., Aida, K., and Urano, A., "Characterization and localization of mRNA encoding the salmon-type gonadotrophin-releasing hormone precursor . . . " Journal of Molecular Endocrinology, Journal of Endocrinology Ltd. (Great Britain), p. 73-82, (Jun. 11, 1992).

Tobet, S.A., Nozaki, M., Youson, J.H., and Sower, S.A., "Distribution of lamprey gonadotropin-releasing hormone-III (GnRH-III) in brains of larval lampreys (Petromyzon marinus)," Cell & Tissue Research, Springer-Verlag (USA), p. 261-270, (Jun. 11, 1995).

Wang, L., Yoo, M.S., Kang, H.M., IM, W.B., Choi, H.S., Bogerd, J., and Kwon, H.B., "Cloning and Characterization of cDNAs Encoding the GnRHI and GnRH2 Precursors From Bullfrog (Rana catesbeiana)," Journal of Experimental Zoology, Wiley-Liss, Inc. (USA), p. 190-201, (Jun. 11, 2001).

Wetsel, W.C., et al., "Metabolism of Pro-Luteinizing . . . ," Endocrinology, The Endocrine Society (USA), vol. 129 (No. 3), p. 1584-95, (Jun. 1991).

White, R.B., Eisen, and Fernald, R.D., "Genomic Structure and Expression Sites of Three Gonadotropin-Releasing Hormone Genes in One Species," General and Comparative Endocrinology, Academic Press (USA), p. 17-25, (Jun. 11, 1998).

White, R.B., Eisen, J.A., Kasten, T.L., and Fernald, R.D., "A second gene for gonadotropin-releasing hormone: cDNA and expression pattern in the brain," Proc. National Academy of Science, p. 1423-27, (Feb. 11, 1994).

White, S.A., Bond, C.T., Francis, R.C., Kasten, T.I., Fernald, R.D., and Adelman, J.P., "A second gene for gonadotropin-releasing hormone: cDNA and expression pattern in the brain," Proc. National Academy of Science, p. 1423-27, (Feb. 11, 1994).

White, S.A., Kasten, T.L., Bond, C.T., Adelman, J.P., and Fernald, R.D., "Three gonadotropin-releasing hormone genes in one organism suggest novel roles for an ancient peptide," Proc. National Academy of Science, p. 8363-67, (Aug. 11, 1995).

Urbanski, H.F., White. R..B., Fernald, R.D.. Kohama, S.G., Garyfallou. V.T., and Densmore, V.S., "Regional Expression of mRNA Encoding a Second Form of Gonadotropin-Releasing Hormone . . . " Endocrinology, The Endocrine Society (USA). vol. 140 (No. 4), p. 1945-48, (Jun. 11, 1999).

Wright, G.M., McBurney, K.M., Youson, J.H., and Sower, S.A., "Distribution of lamprey gonadotropin-releasing hormone in the brain and pituitary gland of larval, metamorphic, and adult sea lampreys, Petromyzon marinus," Can. J. Zool., p. 48-53, (Jun. 11, 1994).

Yoo, M.S., Kang, H.M., Choi H.S., Kim. J.W., Troskie. B.F., <II.I. AR, R.P., and Kwon, H.B., "Molecular cloning, distribution and pharmacological characterization of a novel gonadotropin-releasing . . . " Molecular and Cellular Endocrinology, Elsevier Science Ireland Ltd. (USA). p. 197-204. (Jun. 11, 2000).

Youson, J.H., and Sower, S.A., "Concentration of Gonadotropin-Releasing Hormone in the Brain During Metamorphosis int he Lamprey, Petromyzon marinus," The Journal of Experimental Zoology, Wiley-Liss-Inc. (USA), p. 399-404, (Jun. 11, 1991).

Zmora, N., Gonzalez-Martinez, D., Munoz-Cueto, J.A., Madigou, T., Manonos-Sanchez, E., Doste, S.Z., Zohar, Y., Kah, O., and Elizur, A., "The GnRH system int he European sea bass (Dicentrarchus labrax)," Journal of Endocrinology, Socity for Endocrinology (USA), p. 105-16, (Jun. 11, 2002).

Zohar, Y., Goren, A., Tosky, M., Pagelson, G., Leibovitz, D., and Koch, Y., "The bioactivity of gonadotropin releasing hormones and its regulation in the gilthead seabream, Sparus aurata: in vivo and in vitro studies," Fish Physiology and Biochemistry, Kugler Publications (USA), vol. 7 (No. 1-4), p. 59-67, (Jun. 11, 1989).

* cited by examiner

*G. australis:*

Nucleotide Sequence
GAAAAGCAAANCGATTCCGCTCCGAGCCGCGTTGAGTTTCTCAGNTGTGGTTGATTTTTCCNC
CGATTGGACCCCTCCGGGCATCATCCAGGATCCGCTTGCTGCTGCTNGAGAGAGACAGAGATG
GCACTGCGCGCTCAAAGTCTGGCGCTGGTGCTGTTGTCGGCCTCGGCTTTACTGGTCTCGCTGA
CGCACTCACAACATTGGTCCCACGACTGGAAACCCGGAGGAAAACGCAACCTGGAGGCCATG
AGACCACTGCTGGAGCAGGAGCTGGAACCGCCGAGCGGCGCGTTTGACTGTGACGGACCGGA
ATGCGCGTTTGGTCGGGTTCCGAGCGGCGAGCTCATCCGGGAGATTGTGAGCTACCTCTCGCA
GAAAAACTTTCAAAGAAAGGTTCTGAAATAAAAGCGTCGCATCTCCGGCCGCGGATGAAGAC
AATCAACGCTCCGACAACTCGAGATAATCCCTCTCTTAAGAGCACCGCGTGACACGAACCCGT
CCAGCGAGAGCCCTTTTAATTCATCGTCTTAACACGTGTTGTGTGCCCCGTGACGTCTCGTACA
GACACTCCGCGTTACGTATACAATGAATCGCCGCTCAGCGTATCGTAAACATGATCATGACCG
TGTGTGTGTTTATGTGTGCCGTGCATAGTGCAATGTTCCAGAGTGGCTGTGTGTATGTAGGTGG
GCTACACTTCGTTGTCGGTCATATGAGCCACGTGTACAACAAGGCGGGTGTTGTCCGTGAATA
AAGTTGTCATTAAGCGATAAAAAAAAAAAAAAA Amino Acid Sequence
MALRAQSLALVLLSASALLVSLTHSQHWSHDWKPGGKRNLEAMRPLLEQELEPPSGAFDCDGPE
CAFGRVPSGELIREIVSYLSQKNFQRKVLK

FIG. 1A

*M mordax:*

Nucleotide Sequence
GAACAGAGAGCGATTCCCCCGGCAGCGGTTCTCGCCGTGGTTCGCTTTTCTCCGATACACCTT
GCAGGAATCATCACCGCAGCGATGGCACCGCGCGCTCAAAGCCTGGCGCTGCTGCTGTTGGTC
TCGGCGCTGCTCGTCTCGCCGACACACTCGCAACACTGGACGCACGACTGGAAACCCGGAGG
CAAGCGCGACGTGGACGCCACGAGACCACTGCTCGAGGAGCTGGAACCTCCGAGCAGCGCGT
TCGACTGCGATGGAGCCGATTGCGCCTTCGCTCGGGTTCCCAGCAGCGAACTCATTCGCGACC
TCCTCAGTTACCTCTCGCAGAAGAATCACCAAAGGAAAGTCGTGAAGTGAGAAGCCTCGCAT
CTCCAGCTGCGGATGAAGACAATCAACCCTCCAACTCGATTATTCCCTCGAAGAGCACCGCGC
CACACGAGCACCATTTCTCCATCGTCTCAACACGTGTCATGGTCTGTGACGTCTCGTATTGGCA
CACGCCGTGTCTCGCGTAGAACATTCATACATGCTCATGACCGTATACGTGTATATGTACCGT
ACGTAGTACCATGTTTCCAGAGTGGCTGTGTGTAGGTTTGCCGGTCATACGAATCACGTGTAC
AATGGAGTGTTGCCCCATGAATAAAGTTGTTGCAAGCGAAAAAAAAAA Amino Acid Sequence
MAPRAQSLALLPLVSPTHSQHWSHDWKPGGKRDVDATRPLLEELEPPSSAFDCDGADCAF
ARVPSSELIRDLLSYLSQKNHQRKVVK

FIG. 1B

*L tridentatus:*

Nucleotide Sequence
AAACAAACATTCTCCCTCTCCGAGCTCGTCTTCGCGCGGTGGTTTATTTTCTCAACAGACCGTC
TGGAATCATCGCAGGTGAGCGCCTTCGTTCANAAGCCACACTCGGCTGCTGTAGAGATGGCAC
TGCGCGGTCAAAGTCTGGCTCTGCTGCTGCTCGCGTCGGCGCTGCTCGTGTCGCTGACACACA
CACAGCACTGGTCCCACGACTGGAAACCCGGAGGGAAACGCGACCTGGAGGCCATGAGACCA
CTGCTGGAGGAGCTTGAGGCACCGGACAGCGCGTTCGAATGCGACGGACCCGAATGCGCCTT
CGCTCGAGTGCCGACCAGTGAGCTCGTCAGGGAGATCGTGAGTTACCTCTCGCAGAAGAATTA
TCAAAGGAAAGTTCTGAAGTAAAAGCCCCGCGTCTGAAGCTGCAGATGAAGACAATCAACGC
TCCCGACAATTCGAGAAGTTTCCTCGAGAGCGCCACGTGACGCGAACCCAGTCAATGAAATG
CCCTCGCTGTGGTTTGTGACGTCTCTTAGACCCTTTGTGTTTATTTAATTCTTCATCGCCGCTCA
GCGTATCGTCAACATGACCGTGACCATGTGCGTTTATGTGCACCATACATAGTAGCGTGTCCC
AGAGTGGCTGTGTGTAGGTGGCGTACACTTTGTTATTATTGGTCACGAACAGGCCACGCGTAA
CAACAAGGCGTTGTCCGTGAATAAAGTTGTTATAAGCGATAAAAAAAAAAAAAAAAAA Amino Acid Sequence
MALRGQSLALLLLASALLVSLTHTQHWSHDWKPGGKRDLEAMRPLLEELEAPDSAFECDGPECA
FARVPTSELVREIVSYLSQKNYQRKVLK

FIG. 1C

*P marinus:*

Nucleotide Sequence
CAACTACCGAAACAGATTCCTCTCCGAGCTCGTCTTCGCGCGGTGGTTTATTTTCTCAACAGAC
CGTCTGGAATCATCACAGAAGCCACACTCGGCTGCTGTAGAGATGGCACTGCGCGGTCAAAG
CCTGGTTCTGCTGCTGCTGGCGTCGGCGCTGCTGGTGTCGCTGACGCACACACAGCACTGGTC
CCACGACTGGAAACCCGGAGGGAAACGCGACCTGGAGGCCATGAGACCACTGCTGGAGGAG
GAGCTTGAGGCGCCGAACAGCGCGTTCGAATGCGACGGACCCGAATGCGCCTTCGCTCGAGT
GCCGACTGGTGAGCTCGTCAGGGAGATCGTGAGTTACCTCTCGCAGAAGAATTATCAAAGGA
AAGTTCTGAAGTAAAAGCCCCGCGTCTCAAGCTGCAGATGAAGACAATCAACGCTCCCGACA
ATTCGAGAAGTTCCTCGAGAGCGCCACGTGACACGAACCCTGTCAATGAAATGCCCTCGCTGT
GGTCTGTGACGTCTCTTAGACCCTTTGTGTTTATTTAATTCTTCATCGCCGCTCAGCGTATCGTC
AACATGACCGTGGCCATATGCGTTTATGTGCACCATACATAGTACCGTGTTCCAGAGTGGCTG
TGTGTAGGTGGCGTACACTTTGTTATTATTGGTCACGAACAGGCCACGCGTAACAACAAGGCG
TTGTCCGTGAATAAAGTTGTTATAAGCG Amino Acid Sequence
MALRGQSLVLLLLASALLVSLTHTQHWSHDWKPGGKRDLEAMRPLLEEELEAPNSAFECDGPEC
AFARVPTGELVREIVSYLSQKNYQRKVLK

SEQUENCE LISTING

```
<160> NUMBER OF SEQ ID NOS: 37

<210> SEQ ID NO 1
<211> LENGTH: 790
<212> TYPE: DNA
<213> ORGANISM: g. australis
<220> FEATURE:
<221> NAME/KEY: mat_peptide
```

```
<222> LOCATION: (199)..()
<223> OTHER INFORMATION:
<220> FEATURE:
<221> NAME/KEY: CDS
<222> LOCATION: (124)..(405)
<223> OTHER INFORMATION:

<400> SEQUENCE: 1
gaaaagcaaa gcgattccgc tccgagccgc gttgagtttc tcagttgtgg ttgattttttc      60 caccgattgg acccctccgg gcatcatcca ggatccgctt gctgctgctc gagagagaca     120 gag atg gca ctg cgc gct caa agt ctg gcg ctg gtg ctg ttg tcg gcc       168
    Met Ala Leu Arg Ala Gln Ser Leu Ala Leu Val Leu Leu Ser Ala
        -25             -20                 -15 tcg gct tta ctg gtc tcg ctg acg cac tca caa cat tgg tcc cac gac       216
Ser Ala Leu Leu Val Ser Leu Thr His Ser Gln His Trp Ser His Asp
-10              -5               -1  1                  5 tgg aaa ccc gga gga aaa cgc aac ctg gag gcc atg aga cca ctg ctg       264
Trp Lys Pro Gly Gly Lys Arg Asn Leu Glu Ala Met Arg Pro Leu Leu
            10                  15                  20 gag cag gag ctg gaa ccg ccg agc ggc gcg ttt gac tgt gac gga ccg       312
Glu Gln Glu Leu Glu Pro Pro Ser Gly Ala Phe Asp Cys Asp Gly Pro
        25                  30                  35 gaa tgc gcg ttt ggt cgg gtt ccg agc ggc gag ctc atc cgg gag att       360
Glu Cys Ala Phe Gly Arg Val Pro Ser Gly Glu Leu Ile Arg Glu Ile
    40                  45                  50 gtg agc tac ctc tcg cag aaa aac ttt caa aga aag gtt ctg aaa           405
Val Ser Tyr Leu Ser Gln Lys Asn Phe Gln Arg Lys Val Leu Lys
55                  60                  65 taaaagcgtc gcatctccgg ccgcggatga agacaatcaa cgctccgaca actcgagata     465
atccctctct taagagcacc gcgtgacacg aacccgtcca gcgagagccc ttttaattca     525
tcgtcttaac acgtgttgtg tgccccgtga cgtctcgtac agacactccg cgttacgtat     585
acaatgaatc gccgctcagc gtatcgtaaa catgatcatg accgtgtgtg tgtttatgtg     645
tgccgtgcat agtgcaatgt tccagagtgg ctgtgtgtat gtaggtgggc tacacttcgt     705
tgtcggtcat atgagccacg tgtacaacaa ggcgggtgtt gtccgtgaat aaagttgtca     765
ttaagcgata aaaaaaaaaa aaaaa                                           790

<210> SEQ ID NO 2
<211> LENGTH: 94
<212> TYPE: PRT
<213> ORGANISM: g. australis

<400> SEQUENCE: 2

Met Ala Leu Arg Ala Gln Ser Leu Ala Leu Val Leu Leu Ser Ala Ser
-25                 -20                 -15                 -10

Ala Leu Leu Val Ser Leu Thr His Ser Gln His Trp Ser His Asp Trp
                -5              -1   1                   5

Lys Pro Gly Gly Lys Arg Asn Leu Glu Ala Met Arg Pro Leu Leu Glu
            10                  15                  20

Gln Glu Leu Glu Pro Pro Ser Gly Ala Phe Asp Cys Asp Gly Pro Glu
        25                  30                  35

Cys Ala Phe Gly Arg Val Pro Ser Gly Glu Leu Ile Arg Glu Ile Val
40                  45                  50                  55

Ser Tyr Leu Ser Gln Lys Asn Phe Gln Arg Lys Val Leu Lys
                60                  65

<210> SEQ ID NO 3
```

```
<211> LENGTH: 676
<212> TYPE: DNA
<213> ORGANISM: m. mordax
<220> FEATURE:
<221> NAME/KEY: CDS
<222> LOCATION: (85)..(360)
<223> OTHER INFORMATION:
<220> FEATURE:
<221> NAME/KEY: mat_peptide
<222> LOCATION: (157)..()
<223> OTHER INFORMATION:

<400> SEQUENCE: 3
```

| | | |
|---|---|---|
| gaacagagag cgattccccc ggcagcggtt ctcgccgtgg ttcgcttttc tccgatacac | | 60 |
| cttgcaggaa tcatcaccgc agcg atg gca ccg cgc gct caa agc ctg gcg | | 111 |
|                                       Met Ala Pro Arg Ala Gln Ser Leu Ala<br>                                                                                 -20 | | |

```
ctg ctg ctg ttg gtc tcg gcg ctg ctc gtc tcg ccg aca cac tcg caa      159
Leu Leu Leu Leu Val Ser Ala Leu Leu Val Ser Pro Thr His Ser Gln
-15                 -10                 -5                  -1   1 cac tgg acg cac gac tgg aaa ccc gga ggc aag cgc gac gtg gac gcc      207
His Trp Thr His Asp Trp Lys Pro Gly Gly Lys Arg Asp Val Asp Ala
                5                   10                  15 acg aga cca ctg ctc gag gag ctg gaa cct ccg agc agc gcg ttc gac      255
Thr Arg Pro Leu Leu Glu Glu Leu Glu Pro Pro Ser Ser Ala Phe Asp
            20                  25                  30 tgc gat gga gcc gat tgc gcc ttc gct cgg gtt ccc agc agc gaa ctc      303
Cys Asp Gly Ala Asp Cys Ala Phe Ala Arg Val Pro Ser Ser Glu Leu
        35                  40                  45 att cgc gac ctc ctc agt tac ctc tcg cag aag aat cac caa agg aaa      351
Ile Arg Asp Leu Leu Ser Tyr Leu Ser Gln Lys Asn His Gln Arg Lys
50                  55                  60                  65 gtc gtg aag tgagaagcct cgcatctcca gctgcggatg aagacaatca              400
Val Val Lys accctccaac tcgattattc cctcgaagag caccgcgcca cacgagcacc atttctccat    460
cgtctcaaca cgtgtcatgg tctgtgacgt tcgtattgg cacacgccgt gtctcgcgta     520
gaacattcat acatgctcat gaccgtatac gtgtatatgt accgtacgta gtaccatgtt    580
tccagagtgg ctgtgtgtag gtttgccggt catacgaatc acgtgtacaa tggagtgttg    640
ccccatgaat aaagttgttg caagcgaaaa aaaaaa                              676
```

```
<210> SEQ ID NO 4
<211> LENGTH: 92
<212> TYPE: PRT
<213> ORGANISM: m. mordax

<400> SEQUENCE: 4

Met Ala Pro Arg Ala Gln Ser Leu Ala Leu Leu Leu Leu Val Ser Ala
            -20                 -15                 -10

Leu Leu Val Ser Pro Thr His Ser Gln His Trp Thr His Asp Trp Lys
        -5                  -1   1                   5

Pro Gly Gly Lys Arg Asp Val Asp Ala Thr Arg Pro Leu Leu Glu Glu
    10                  15                  20

Leu Glu Pro Pro Ser Ser Ala Phe Asp Cys Asp Gly Ala Asp Cys Ala
25                  30                  35                  40

Phe Ala Arg Val Pro Ser Ser Glu Leu Ile Arg Asp Leu Leu Ser Tyr
                45                  50                  55

Leu Ser Gln Lys Asn His Gln Arg Lys Val Val Lys
            60                  65
```

-continued

```
<210> SEQ ID NO 5
<211> LENGTH: 750
<212> TYPE: DNA
<213> ORGANISM: l. tridentatus
<220> FEATURE:
<221> NAME/KEY: mat_peptide
<222> LOCATION: (193)..()
<223> OTHER INFORMATION:
<220> FEATURE:
<221> NAME/KEY: CDS
<222> LOCATION: (121)..(396)
<223> OTHER INFORMATION:

<400> SEQUENCE: 5
aaacaaacat tctccctctc cgagctcgtc ttcgcgcggt ggtttatttt ctcaacagac      60
cgtctggaat catcgcaggt gagcgccttc gttcagaagc cacactcggc tgctgtagag    120 atg gca ctc cgc ggt caa agt ctg gct ctg ctg ctc gcg tcg gcg           168
Met Ala Leu Arg Gly Gln Ser Leu Ala Leu Leu Leu Ala Ser Ala
            -20                 -15                 -10 ctg ctc gtg tcg ctg aca cac aca cag cac tgg tcc cac gac tgg aaa      216
Leu Leu Val Ser Leu Thr His Thr Gln His Trp Ser His Asp Trp Lys
         -5                  -1  1                   5 ccc gga ggg aaa cgc gac ctg gag gcc atg aga cca ctg ctg gag gag      264
Pro Gly Gly Lys Arg Asp Leu Glu Ala Met Arg Pro Leu Leu Glu Glu
         10                  15                  20 ctt gag gca ccg gac agc gcg ttc gaa tgc gac gga ccc gaa tgc gcc      312
Leu Glu Ala Pro Asp Ser Ala Phe Glu Cys Asp Gly Pro Glu Cys Ala
25                  30                  35                  40 ttc gct cga gtg ccg acc agt gag ctc gtc agg gag atc gtg agt tac      360
Phe Ala Arg Val Pro Thr Ser Glu Leu Val Arg Glu Ile Val Ser Tyr
                 45                  50                  55 ctc tcg cag aag aat tat caa agg aaa gtt ctg aag taaaagcccc           406
Leu Ser Gln Lys Asn Tyr Gln Arg Lys Val Leu Lys
                 60                  65 gcgtctgaag ctgcagatga agacaatcaa cgctcccgac aattcgagaa gtttcctcga    466
gagcgccacg tgacgcgaac ccagtcaatg aaatgccctc gctgtggttt gtgacgtctc    526
ttagacccct tgtgtttatt taattcttca tcgccgctca gcgtatcgtc aacatgaccg    586
tgaccatgtg cgtttatgtg caccatacat agtagcgtgt cccagagtgg ctgtgtgtag    646
gtggcgtaca ctttgttatt attggtcacg aacaggccac gcgtaacaac aaggcgttgt    706
ccgtgaataa agttgttata agcgataaaa aaaaaaaaa aaaa                      750

<210> SEQ ID NO 6
<211> LENGTH: 92
<212> TYPE: PRT
<213> ORGANISM: l. tridentatus

<400> SEQUENCE: 6

Met Ala Leu Arg Gly Gln Ser Leu Ala Leu Leu Leu Ala Ser Ala
            -20                 -15                 -10

Leu Leu Val Ser Leu Thr His Thr Gln His Trp Ser His Asp Trp Lys
         -5                  -1  1                   5

Pro Gly Gly Lys Arg Asp Leu Glu Ala Met Arg Pro Leu Leu Glu Glu
         10                  15                  20

Leu Glu Ala Pro Asp Ser Ala Phe Glu Cys Asp Gly Pro Glu Cys Ala
25                  30                  35                  40

Phe Ala Arg Val Pro Thr Ser Glu Leu Val Arg Glu Ile Val Ser Tyr
                 45                  50                  55
```

```
Leu Ser Gln Lys Asn Tyr Gln Arg Lys Val Leu Lys
        60                  65
```

```
<210> SEQ ID NO 7
<211> LENGTH: 718
<212> TYPE: DNA
<213> ORGANISM: p. marinus
<220> FEATURE:
<221> NAME/KEY: CDS
<222> LOCATION: (107)..(385)
<223> OTHER INFORMATION:
<220> FEATURE:
<221> NAME/KEY: mat_peptide
<222> LOCATION: (179)..()
<223> OTHER INFORMATION:

<400> SEQUENCE: 7
```

```
caactaccga aacagattcc tctccgagct cgtcttcgcg cggtggttta ttttctcaac     60
agaccgtctg gaatcatcac agaagccaca ctcggctgct gtagag atg gca ctg      115
                                                   Met Ala Leu cgc ggt caa agc ctg gtt ctg ctg ctg gcg tcg gcg ctg ctg gtg        163
Arg Gly Gln Ser Leu Val Leu Leu Leu Ala Ser Ala Leu Leu Val
    -20             -15                 -10 tcg ctg acg cac aca cag cac tgg tcc cac gac tgg aaa ccc gga ggg    211
Ser Leu Thr His Thr Gln His Trp Ser His Asp Trp Lys Pro Gly Gly
-5              -1  1               5                   10 aaa cgc gac ctg gag gcc atg aga cca ctg ctg gag gag gag ctt gag    259
Lys Arg Asp Leu Glu Ala Met Arg Pro Leu Leu Glu Glu Glu Leu Glu
            15                  20                  25 gcg ccg aac agc gcg ttc gaa tgc gac gga ccc gaa tgc gcc ttc gct    307
Ala Pro Asn Ser Ala Phe Glu Cys Asp Gly Pro Glu Cys Ala Phe Ala
        30                  35                  40 cga gtg ccg act ggt gag ctc gtc agg gag atc gtg agt tac ctc tcg    355
Arg Val Pro Thr Gly Glu Leu Val Arg Glu Ile Val Ser Tyr Leu Ser
    45                  50                  55 cag aag aat tat caa agg aaa gtt ctg aag taaaagcccc gcgtctcaag      405
Gln Lys Asn Tyr Gln Arg Lys Val Leu Lys
60                  65 ctgcagatga agacaatcaa cgctcccgac aattcgagaa gttcctcgag agcgccacgt    465
gacacgaacc ctgtcaatga aatgccctcg ctgtggtctg tgacgtctct tagacccttt    525
gtgtttattt aattcttcat cgccgctcag cgtatcgtca acatgaccgt ggccatatgc    585
gtttatgtgc accatacata gtaccgtgtt ccagagtggc tgtgtgtagg tggcgtacac    645
tttgttatta ttggtcacga acaggccacg cgtaacaaca aggcgttgtc cgtgaataaa    705
gttgttataa gcg                                                        718
```

```
<210> SEQ ID NO 8
<211> LENGTH: 93
<212> TYPE: PRT
<213> ORGANISM: p. marinus

<400> SEQUENCE: 8

Met Ala Leu Arg Gly Gln Ser Leu Val Leu Leu Leu Ala Ser Ala
                    -20                 -15                 -10

Leu Leu Val Ser Leu Thr His Thr Gln His Trp Ser His Asp Trp Lys
            -5              -1  1               5

Pro Gly Gly Lys Arg Asp Leu Glu Ala Met Arg Pro Leu Leu Glu Glu
        10                  15                  20

Glu Leu Glu Ala Pro Asn Ser Ala Phe Glu Cys Asp Gly Pro Glu Cys
25                  30                  35                  40
```

Ala Phe Ala Arg Val Pro Thr Gly Glu Leu Val Arg Glu Ile Val Ser
                45                  50                  55

Tyr Leu Ser Gln Lys Asn Tyr Gln Arg Lys Val Leu Lys
                60                  65

<210> SEQ ID NO 9
<211> LENGTH: 21
<212> TYPE: DNA
<213> ORGANISM: g. australis

<400> SEQUENCE: 9
ggctctcgct ggacgggttc g                                    21

<210> SEQ ID NO 10
<211> LENGTH: 24
<212> TYPE: DNA
<213> ORGANISM: m. mordax

<400> SEQUENCE: 10
ctgcgagagg taactgagga ggtc                                 24

<210> SEQ ID NO 11
<211> LENGTH: 22
<212> TYPE: DNA
<213> ORGANISM: p. marinus

<400> SEQUENCE: 11
ggcgctctcg aggaacttct cg                                   22

<210> SEQ ID NO 12
<211> LENGTH: 27
<212> TYPE: DNA
<213> ORGANISM: l. tridentatus

<400> SEQUENCE: 12
cctacacaca gccactctgg gacacgc                              27

<210> SEQ ID NO 13
<211> LENGTH: 24
<212> TYPE: DNA
<213> ORGANISM: g. australis

<400> SEQUENCE: 13
gattccgctc cgagccgcgt tgag                                 24

<210> SEQ ID NO 14
<211> LENGTH: 23
<212> TYPE: DNA
<213> ORGANISM: g. australis

<400> SEQUENCE: 14
ccgacaacga agtgtagccc acc                                  23

<210> SEQ ID NO 15
<211> LENGTH: 23
<212> TYPE: DNA
<213> ORGANISM: m. mordax

<400> SEQUENCE: 15
gcagcggttc tcgccgtggt tcg                                  23

<210> SEQ ID NO 16

```
<211> LENGTH: 26
<212> TYPE: DNA
<213> ORGANISM: m. mordax

<400> SEQUENCE: 16
ggcaaaccta cacacagcca ctctgg                                              26

<210> SEQ ID NO 17
<211> LENGTH: 26
<212> TYPE: DNA
<213> ORGANISM: p. marinus

<400> SEQUENCE: 17
gaccgtctgg aatcatcaca gaagcc                                              26

<210> SEQ ID NO 18
<211> LENGTH: 22
<212> TYPE: DNA
<213> ORGANISM: p. marinus

<400> SEQUENCE: 18
ggccttgttg ttacgcgtgg cc                                                  22

<210> SEQ ID NO 19
<211> LENGTH: 27
<212> TYPE: DNA
<213> ORGANISM: l. tridentatus

<400> SEQUENCE: 19
caacagaccg tctggaatca tcgcagg                                             27

<210> SEQ ID NO 20
<211> LENGTH: 27
<212> TYPE: DNA
<213> ORGANISM: l. tridentatus

<400> SEQUENCE: 20
cctacacaca gccactctgg gacacgc                                             27

<210> SEQ ID NO 21
<211> LENGTH: 21
<212> TYPE: DNA
<213> ORGANISM: lamprey
<220> FEATURE:
<221> NAME/KEY: misc_feature
<222> LOCATION: (12)..(12)
<223> OTHER INFORMATION: A degenerate primer.  Is used to cover all
      possibilities at that location.

<400> SEQUENCE: 21
garcaytggt cncacgattg g                                                   21

<210> SEQ ID NO 22
<211> LENGTH: 25
<212> TYPE: DNA
<213> ORGANISM: universal

<400> SEQUENCE: 22
aactggaaga attcgcccgg aggaa                                               25

<210> SEQ ID NO 23
<211> LENGTH: 10
<212> TYPE: PRT
<213> ORGANISM: mammal
<220> FEATURE:
```

```
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 23

Xaa His Trp Ser Tyr Gly Leu Arg Pro Xaa
1               5                   10

<210> SEQ ID NO 24
<211> LENGTH: 10
<212> TYPE: PRT
<213> ORGANISM: guinea pig
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 24

Xaa Tyr Trp Ser Tyr Gly Val Arg Pro Xaa
1               5                   10

<210> SEQ ID NO 25
<211> LENGTH: 10
<212> TYPE: PRT
<213> ORGANISM: chicken
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 25

Xaa His Trp Ser Tyr Gly Leu Gln Pro Xaa
1               5                   10

<210> SEQ ID NO 26
<211> LENGTH: 10
<212> TYPE: PRT
<213> ORGANISM: rana
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 26

Xaa His Trp Ser Tyr Gly Leu Trp Pro Xaa
1               5                   10

<210> SEQ ID NO 27
<211> LENGTH: 10
<212> TYPE: PRT
<213> ORGANISM: seabream
<220> FEATURE:
<221> NAME/KEY: MISC_FEATURE
<222> LOCATION: (1)..(1)
<223> OTHER INFORMATION: X at position 1 = pGlu
```

```
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 27

Xaa His Trp Ser Tyr Gly Leu Ser Pro Xaa
1               5                   10

<210> SEQ ID NO 28
<211> LENGTH: 10
<212> TYPE: PRT
<213> ORGANISM: salmon
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 28

Xaa His Trp Ser Tyr Gly Trp Leu Pro Xaa
1               5                   10

<210> SEQ ID NO 29
<211> LENGTH: 10
<212> TYPE: PRT
<213> ORGANISM: medaka
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 29

Xaa His Trp Ser Phe Gly Leu Ser Pro Xaa
1               5                   10

<210> SEQ ID NO 30
<211> LENGTH: 10
<212> TYPE: PRT
<213> ORGANISM: catfish
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 30

Xaa His Trp Ser His Gly Leu Asn Pro Xaa
1               5                   10

<210> SEQ ID NO 31
<211> LENGTH: 10
<212> TYPE: PRT
<213> ORGANISM: herring
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
```

```
<223> OTHER INFORMATION: X at position 10 = Gly-NH2

<400> SEQUENCE: 31

Xaa His Trp Ser His Gly Leu Ser Pro Xaa
1               5                   10

<210> SEQ ID NO 32
<211> LENGTH: 10
<212> TYPE: PRT
<213> ORGANISM: chicken
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 32

Xaa His Trp Ser His Gly Trp Tyr Pro Xaa
1               5                   10

<210> SEQ ID NO 33
<211> LENGTH: 10
<212> TYPE: PRT
<213> ORGANISM: dogfish
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 33

Xaa His Trp Ser His Gly Trp Leu Pro Xaa
1               5                   10

<210> SEQ ID NO 34
<211> LENGTH: 10
<212> TYPE: PRT
<213> ORGANISM: lamprey
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 34

Xaa His Tyr Ser Leu Glu Trp Lys Pro Xaa
1               5                   10

<210> SEQ ID NO 35
<211> LENGTH: 10
<212> TYPE: PRT
<213> ORGANISM: lamprey
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 35
```

```
Xaa His Trp Ser His Asp Trp Lys Pro Xaa
1               5                   10

<210> SEQ ID NO 36
<211> LENGTH: 10
<212> TYPE: PRT
<213> ORGANISM: tunicate
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 36

Xaa His Trp Ser Asp Tyr Phe Lys Pro Xaa
1               5                   10

<210> SEQ ID NO 37
<211> LENGTH: 10
<212> TYPE: PRT
<213> ORGANISM: tunicate
<220> FEATURE:
<221> NAME/KEY: MISC_FEATURE
<222> LOCATION: (1)..(1)
<223> OTHER INFORMATION: X at position 1 = pGlu
<220> FEATURE:
<221> NAME/KEY: MISC_FEATURE
<222> LOCATION: (10)..(10)
<223> OTHER INFORMATION: X at position 10 = Gly-NH2

<400> SEQUENCE: 37

Xaa His Trp Ser Leu Cys His Ala Pro Xaa
1               5                   10
```

LAMPREY GNRH-III POLYPEPTIDES AND METHODS OF MAKING THEREOF

CROSS-REFERENCE TO RELATED APPLICATIONS

The present application is a divisional of patent application Ser. No. 10/170,096 filed on Jun. 12, 2002, now U.S. Pat. No. 6,949,365 issued Sep. 27, 2005, which is incorporated herein by reference.

GOVERNMENT SPONSORSHIP

This Invention is funded in part by NICHD grant No. R03 HD39166-02; NSF IBN0090852; and NSF INT-981528.

COPYRIGHT

A portion of the disclosure of this patent document contains material which is subject to copyright protection. The copyright owner has no objection to the facsimile reproduction by anyone of the patent document or the patent disclosure as it appears in the United States Patent and Trademark Office patent file or records, but otherwise reserves all copyright rights whatsoever.

FIELD OF THE INVENTION

The invention relates to novel forms of GnRH in Lamprey, in particular, an isolated cDNA encoding the precursor of a novel form of gonadotropin-releasing hormone in lamprey and the isolated polypeptides encoded thereby and a method of making thereof.

BACKGROUND OF THE INVENTION

GnRH

In vertebrates, the hypothalamus and pituitary have well-defined roles in the control of reproduction. GnRH (gonadotropin-releasing hormone) is the central regulatory neurohormone controlling reproduction in all vertebrates. GnRH is a ten amino-acid peptide, synthesized in the hypothalamus and released into the hypophysial portal blood system, directly into the pituitary gland as in the case of teleost fish, or by diffusion as in the case of agnathans. Upon response to external cues (for example as environmental cues such as water temperature) and internal cues GnRH is released and acts at the pituitary gland to stimulate the synthesis and release of the gonadotropins, which in turn travel by systemic circulation to the gonads, thereby regulating steroidogenesis and gametogenesis.

GnRH has been the subject of intense research over many years because of its dual significance for understanding reproductive biology and for developing medical therapies. Aside from its importance in research for understanding reproductive biology, GnRH has many medical and other practical applications including reproductive enhancement and/or contraception in animals and fishes. In fact, GnRH and its analogs are already being used in commercial fish farming to stimulate and regulate sexual maturation and reproduction.

Over the past 15 years or so, a considerable amount of research has been devoted to the effects of GnRH and its analogs on reproduction in fish. Many of the economically important fish do not reproduce spontaneously in captivity. Thus manipulation of their reproductive cycles is crucial to marine aquaculture. Almost all of the research to date has been focused on GnRH-based spawning induction therapy in a number of commercially important species (Zohar et al., 1989). Brood females of salmon and other valuable species will spawn in captivity, but have difficulties in their spawning and the timing of spawning. By implanting a GnRH agonist into a brood female, a fish farmer can ensure that the female will ripen at the proper time, thus preventing potentially costly guesswork. However, while there has been considerable success in achieving high yields in rearing fish, there has been only limited success in the manipulation of the reproductive cycles and spawning of the reared fish. In addition, most of the work to date has focused on or examined the ability of GnRH agonists to induce spawning in females. Few researchers have examined the ability of GnRH antagonists to sterilize male fish, due to its lack of commercial application in aquaculture. However, a new method of sterilization would be very useful in the field of sea lamprey control in the Great Lakes.

During the past few years, the Great Lakes Fisheries Commission (GLFC) has been searching for alternative methods to control sea lamprey populations. In its 1992 Strategic Plan, the GLFC stated that one of its major objectives was to suppress sea lamprey populations to target levels by reduction of the use of lampricides and by development of new control methods by 2010. A compound called Bisazir is currently being used in a sterile-male release program. This compound is extremely hazardous to humans, however, and required a special facility to be constructed at Hammond Bay Biological Station, MI in 1991 for its use. Other chemosterilants that are non-hazardous need to be developed. Although some have suggested inhibiting gonadal development by the negative regulation of GnRH, there have not been any viable methods developed. See U.S. Pat. No. 6,210,927 to Zohar, which is incorporated herein in its entirety, for brief mention of inhibition of gonadal development in fish and examples of some uses and applications for seabream GnRH.

Thus, it would be desirable to have a method of sterilizing male sea lampreys, and other fish or animals, using a lamprey or other appropriate species GnRH antagonist.

There are also many potential therapeutic human reproductive applications for GnRH. Since 1971 when the primary structure of mammalian GnRH was determined, over 7,000 analogs to GnRH have been made and tested in hundreds of studies in mammals. So far, the most active synthetic agonists are found to be those with D-amino acid substitution in position 6 of the GnRH decapeptide. The most effective GnRH antagonists to date are those that have substitutions in position 6 as well as substitution of amino acids in positions 1, 2, and 3.

As a result of these studies several mammalian GnRH analogs have been shown to be highly successful and are currently being used for sterilization, conception and other therapeutic and clinical applications. In fact, the clinical application of GnRH analogs as therapeutic drugs generates over 2 billion dollars per year in sales. Hence there is considerable interest in the function of each residue in the GnRH so that analogs can be designed with maximum efficiency as agonists or antagonists to the GnRH receptor, for use as drugs. Furthermore, the responses to GnRH and analogs are different in males compared to females, suggesting that different neuroendocrine mechanisms may be involved.

To date, many analogs have proven useful, but produce undesirable side effects, such as affecting more than just the target. For example, Lupron Depot® which is a GnRH analog and is now one of the leading chemical treatments for advanced prostate cancer and endometriosis in humans has undesirable side effects. Specifically, continuous treatment of Lupron Depot® results in decreased levels of luteinizing hormone (LH) and follicle stimulating hormone (FSH). In males, testosterone is reduced to castrate levels. In pre-menopausal females, estrogens are reduced to post-menopausal levels.

Thus, there is still critical information that is needed for understanding the biological activity of these analogs. The potential wider use of GnRH antagonists in humans awaits the availability of potent analogs that do not have the side effects (including high histamine releasing activity) seen with currently-used analogs.

Lamprey

GnRH has also been studied in several species in the process of researching the evolution of reproductive biology, one of which species is the lamprey. Lampreys and hagfish of the Class Agnatha are of particular importance in understanding endocrinological relationships since they are the modern descendants of the most primitive vertebrates available for study. They represent the oldest lineages of extant vertebrates—which evolved over 550 million years ago. Therefore, the study of lampreys and the characterization of brain and pituitary hormones in lampreys is particularly important for understanding the molecular evolution and functional diversity of reproductive hormones, and can potentially yield valuable insight into human reproductive processes. As noted above, GnRH is the central regulatory neurohormone controlling reproduction in all vertebrates. However, until about 15 years ago, there was little evidence for neuroendocrine control of reproduction in lampreys.

There are approximately 40 species of lampreys that are classified as parasitic or non-parasitic. Lampreys spawn only once in their lifetimes, after which they die. All larval lampreys, called ammocoetes, live in fresh water as borrowing organisms in the bottoms of streams or lakes. In the parasitic sea lamprey, sexual maturation is a seasonal, synchronized process. The sea lampreys begin their lives as fresh water ammocoetes, which are blind, filter feeding larvae. After approximately 5-7 years in freshwater streams, metamorphosis occurs and the ammocoetes become free-swimming, sexually immature lampreys, which migrate to the sea or lakes. During the approximately 15 month-long parasitic sea phase, gametogenesis progresses. After approximately 15 months at sea, lampreys return to freshwater streams and undergo the final maturational processes resulting in mature eggs and sperm, and finally spawning.

As stated above, however, until about 15 years ago, there was a question as to whether there was brain control of reproduction in lampreys. The question of whether there is hypothalamic control over reproduction in lampreys has special significance, because lampreys are modern descendants of the one of the oldest lineages of extant vertebrates and are among the most primitive vertebrates available for study. Thus, the study of lamprey reproduction can shed light on the overall evolution of vertebrate reproduction.

Currently thirteen structures of GnRH have been determined in various vertebrate species and two in invertebrates. They have traditionally been named for the species from which they were first isolated. Table 1 summarizes the various known forms of the GnRH decapeptide. Also, the history of discovery, isolation and characterization of the various known forms of cDNA sequences encoding GnRH precursors is summarized in Table 2 which lists the characterized cDNA's of GnRH precursors.

Table 1

The 15 known GnRH isoforms, grouped together based on the regions of similarity, with differences from mammalian mGnRH underlined.

TABLE 1

The 15 known GnRH isoforms, grouped together based on the regions of similarity.

| GnRH | 1 | 2 | 3 | 4 | 5 | 6 | 7 | 8 | 9 | 10 |
|---|---|---|---|---|---|---|---|---|---|---|
| Vertebrate | | | | | | | | | | |
| Mammal | pGlu | His | Trp | Ser | Tyr | Gly | Leu | Arg | Pro | Gly-NH$_2$ |
| Guinea Pig | pGlu | Tyr | Trp | Ser | Tyr | Gly | Val | Arg | Pro | Gly-NH$_2$ |
| Chicken - I | pGlu | His | Trp | Ser | Tyr | Gly | Leu | Gln | Pro | Gly-NH$_2$ |
| Rana | pGlu | His | Trp | Ser | Tyr | Gly | Leu | Trp | Pro | Gly-NH$_2$ |
| Seabream | pGlu | His | Trp | Ser | Tyr | Gly | Leu | Ser | Pro | Gly-NH$_2$ |
| Salmon | pGlu | His | Trp | Ser | Tyr | Gly | Trp | Leu | Pro | Gly-NH$_2$ |
| Medaka | pGlu | His | Trp | Ser | Phe | Gly | Leu | Ser | Pro | Gly-NH$_2$ |
| Catfish | pGlu | His | Trp | Ser | His | Gly | Leu | Asn | Pro | Gly-NH$_2$ |
| Herring | pGlu | His | Trp | Ser | His | Gly | Leu | Ser | Pro | Gly-NH$_2$ |
| Chicken -II | pGlu | His | Trp | Ser | His | Gly | Trp | Tyr | Pro | Gly-NH$_2$ |
| Dogfish | pGlu | His | Trp | Ser | His | Gly | Trp | Leu | Pro | Gly-NH$_2$ |
| Lamprey - III | pGlu | His | Trp | Ser | His | Asp | Trp | Lys | Pro | Gly-NH$_2$ |
| Lamprey - I | pGlu | His | Tyr | Ser | Leu | Glu | Trp | Lys | Pro | Gly-NH$_2$ |
| Invertebrate | | | | | | | | | | |
| Tunicate - I | pGlu | His | Trp | Ser | Asp | Tyr | Phe | Lys | Pro | Gly-NH$_2$ |
| Tunicate - II | pGlu | His | Trp | Ser | Leu | Cys | His | Ala | Pro | Gly-NH$_2$ |

The 15 primary structures of GnRH where originally sequenced in pig, mGnRH (Matsuo et al., 1971; Burgus et al., 1972), guinea pig, gpGnRH (Jimenez-Linan et al., 1997), chicken, two forms, chGnRH-I and chGnRH-II (King and Millar, 1982a; King and Millar, 1982b; Miyamoto et al., 1983; Miyamoto et al., 1984), salmon, sGnRH (Sherwood et al., 1983), lamprey, two forms, lGnRH-I and lGnRH-II (Sherwood et al., 1986; Sower et al., 1993), catfish, cfGnRH (Ngamvongchon et al., 1992), dogfish, dGnRH (Lovejoy et al., 1992), herring, hGnRH (Carolsfeld et al., 2000), seabream, sbGnRH (Powell et al., 1994), rana, rGnRH (Yoo et al., 2000), medaka, mdGnRH (Okubo et al., 2000), and tunicate (a protochordate), two forms, tGnRH-I and tGnRH-II (Powell et al., 1996).

Table 2
The history of discovery, isolation and characterization of the various known forms of cDNA sequences encoding GnRH precursors.

| | GnRH cDNAs and Genes | | |
|---|---|---|---|
| Isoform | Organism | Year | Reference |
| Mammalian | Human | 1984 | Seeburg et al., Nature |
| | Norway Rat | 1986 | Adelman et al., PNAS |
| | Mouse | 1986 | Mason et al., Science |
| | Norway Rat | 1989 | Bond et al., Mol Endocrinol |
| | African Clawed Frog | 1994 | Hayes et al., Endo |
| | Tree Shrew | 1995 | White et al., Soc Neurosci |
| | *Haplochromis burtoni* | 1998 | White et al., Gen Comp Endo |
| | Japanese Eel | 1999 | Okubo et al., Zool Sci |
| | Bullfrog | 2001 | Wang et al., J Exp Zool |
| Salmon | Goldfish | 1991 | Bond et al., Mol Endo |
| | Atlantic Salmon | 1992 | Klungland et al., Mol Cell Endo |
| | Rainbow Trout | 1992 | Alestrom et al., Mol Marine Biol Biotechnol |
| | Cherry Salmon | 1992 | Suzukiet at., J Mol Endo |
| | Brook Trout | 1992 | Klungland et al., Mol Cell Endo |
| | Chinook Salmon | 1992 | Klungland et al., Mol Cell Endo |
| | Rainbow Trout | 1992 | Klungland et al., Mol Cell Endo |
| | Brown Trout | 1992 | Klungland et al., Mol Cell Endo |
| | Plainfin Midshipman | 1995 | Grober et al., Gen Comp Endo |
| | Sockeye Salmon | 1995 | Coe et al., Mol Cell Endo |
| | Medaka | 2000 | Okubu et al., Biochem Biophys Res Commun |
| | Australian Bonytongue | 2001 | Okubu and Aida, Gen Comp Endo |
| | European Sea Bass | | Zmora et al., (unpublished) |
| | Zebrafish | | Torgersen et al., (unpublished) |
| | *Verasper moseri* | | Amano (unpublished) |
| Lamprey III | Sea Lamprey | 2002 | Silver et al., Am Zool |
| | Pacific Sea Lamprey | 2002 | Silver et al., Am Zool |
| | Australian Lamprey | 2002 | Silver et al., Am Zool |
| | Pouched Lamprey | 2002 | Silver et al., Am Zool |
| Lamprey I | Sea Lamprey | 2001 | Suzuki et al., J Mol Endo |
| Guinea Pig | Guinea Pig | 1997 | Jimenez-Linan et al., Endo |
| Chicken I | Chicken | 1993 | Dunn et al., J Mol Endo |
| Rana | Frog | 2000 | Yoo et al., Mol Cell Endo |
| Medaka | Medaka | 2000 | Okubu et al., Biochem Biophys Res Commun |
| Catfish | African Catfish | 1994 | Bogerd et al., Eur J Biochem |
| Chicken II | Goldfish | 1994 | Bogerd et al., Eur J Biochem |
| | *Haplochromis burtoni* | 1994 | White et al., PNAS |
| | Tree Shrew | 1995 | White et al., Soc Neurosci |
| | Rhesus Monkey | 1996 | Dong et al., Mol Cell Endo |
| | Human | 1998 | White et al., PNAS |
| | Striped Sea-Bass | 1998 | Chow et al., J Mol Endo |
| | Rhesus Monkey | 1998 | White et al., Soc Neurosci |
| | *Haplochromis burtoni* | 1998 | White et al., Gen Comp Endo |
| | Human | 1998 | White et al., PNAS |
| | Japanese Eel | 1999 | Okubo et al., Zool Sci |
| | Medaka | 2000 | Okubu et al., Biochem Biophys Res Commun |
| | Australian Bonytongue | 2001 | Okubo and Aida, Gen Comp Endo |
| | Bullfrog | 2001 | Wang et al., J Exp Zool |
| | *Verasper moseri* | | Amano (unpublished) |
| | European Sea Bass | | Zmora et al. (unpublished) |
| | Silver-Gray Brushtail Possum | | Lawrence et al. (unpublished) |
| | Rio Cauca Caecilian | | Ebersole et al., (unpublished) |
| | House Shrew | | White et al. (unpublished) |
| Seabream | Sockeye Salmon | 1995 | Ashihara et al., J Mol Endo |
| | Striped Sea-Bass | 1998 | Chow et al., J Mol Endo |
| | *Haplochromis burtoni* | 1998 | White et al., Gen Comp Endo |
| | *Verasper moseri* | | Amano (unpublished) |
| | European Sea Bass | | Zmora et al. (unpublished) |
| | Red Sea Bream | | Okuzawa (unpublished) |

To date, it has been believed that there is only one form of mammalian GnRH that controls the pituitary in mammals. The first GnRH was isolated and characterized from mammals in the early 1970's and is now referred to as mGnRH. However, it is now believed that there are at least two forms of GnRH in all species, which are not just alternative splice variants, but rather are encoded by separate genes (White et al., 1994). The presence of multiple forms of GnRH suggests a functional differentiation, although this has not been characterized.

For example, two main forms of GnRH have been isolated in sea lampreys: lamprey GnRH-I and lamprey GnRH-III. The cDNA (or gene sequence) of lamprey GnRH-I has also been identified, along with cDNA's of eleven of the fifteen known GnRH's in other species. Again, lampreys are studied because they are the most primitive vertebrates for which there are demonstrated functional roles for multiple GnRH neurohormones involved in pituitary-reproductive activity. Thus the study of lamprey can provide insight into higher vertebrate reproduction. Both lamprey GnRH-I and -III have been shown to induce steroidogenesis and spermiation/ovulation in adult sea lampreys (Deragon and Sower, 1994; Gazourian et al., 1997; Sower, 1990; Sower et al., 1993; Sower, 1998).

In studying the various forms of GnRH, which is a ten (10) amino acid protein, the forms most closely related to an ancestral GnRH molecule are most likely the forms present in fishes of ancient origin, for example, lampreys. In all GnRH peptides studied to date, as can be seen from Table 1, certain regions of the molecule have been highly conserved among all species studied, including the NH2-terminal, pGlu1 and Ser4, and the COOH-terminal. The conservation of the NH2- and COOH-termini suggests that these regions are significant for conformation, receptor binding, and resistance to enzymatic degradation, and in receptor-mediated events required for gonadotropin release.

In addition, as can be seen in Table 2, the known cDNA's predict a GnRH consistent with other neuropeptides. The tripartite precursor polypeptide, called prepro-GnRH is synthesized as part of a larger protein which upon post-translational modification yields the mature decapeptide (Klungland et al. 1992). The tripartite prepro-GnRH consists of a leader peptide at the N-terminal hydrophobic signal domain in direct linkage with the GnRH decapeptide; followed by a 3 amino acid dibasic cleavage processing site (GLY-LYS-ARG); and, at the C-terminal end an additional peptide called GnRH associated peptide (GAP). The precursor is processed by cleavage at the dibasic amino acids (LYS-ARG). GnRH and GAP are then stored within the secretory granules until secreted (Wetsel et al., 1991; Endocrinol. 129: 1584-1594).

The mammalian form of GnRH was first isolated form porcine and ovine hypothalamic extracts, giving rise to the popularly held view that only a single form of GnRH is present in all mammals. However, a question that has arisen over the years with respect to mammals is: How does one GnRH differentially regulate the release of two pituitary gonadotropin hormones, LH and FSH? An answer could be found in the fact that, as noted above, in recent years it has been shown that in vertebrates, at least two different forms of GnRH are expressed within the brain, although not necessarily the hypothalamus, of a single species. Generally, where two forms of GnRH have been found, one GnRH is located in the hypothalamus and functions as a neurohormone regulating the pituitary in the control of the gonadotropin release. The second form may have a neurotransmitter or neuromodulatory function and is localized in areas outside the hypothalamus such as in the midbrain regions. In a limited number of mammals a second form of GnRH has been shown to exist, and it is generally extra-hypothalamic. Where two forms of GnRH have been found in a species, it is also believed that separate genes encode for the multiple forms of GnRH (White et al. 1994; Suzuki et al., 2000). In addition, the presence of multiple forms (and locations) of GnRH suggests a functional differentiation (such as differential regulation of FSH and LH), although this has not been characterized.

Based on studies of lampreys and other species in which two forms of GnRH are found, and the high degree of conservation of amino acid sequence between species, study of a known second form of GnRH in one species (for example lampreys) could lead to identification and isolation of a second form of GnRH in other species. If separate genes were found and isolated for multiple forms of GnRH in various species, including primate, and especially human, these findings would have a substantial impact on our understanding of the release of gonadotropins and would be of great value in clinical studies and practical applications.

In addition, the elucidation of the nucleotide sequence of the cDNA's and/or genes of GnRH and other brain hormones in the lamprey is necessary in order to answer questions concerning both comparative analysis of species and the molecular evolution of neuroendocrine hormones in vertebrates. Using such knowledge, in both humans and other species, new GnRH analogs could be developed that may not have the side effects produced with the GnRH analogs currently used in various applications. Study of a novel GnRH in lampreys, and the evolutionary insights yielded therefrom, could lead to discovery of a novel hypothalamic GnRH in mammals which could lead to the formation of new, useful GnRH analogs.

Thus, despite the knowledge of GnRH to date, there remains a need in both marine aquaculture and human medicine for greater knowledge of GnRH and the evolution of neuroendocrine hormones. This knowledge could be used to produce more effective analogs which could better manipulate reproduction in fish, and which could more effectively be used in human therapy, including reproductive and cancer therapy among others.

SUMMARY OF THE INVENTION

In accordance with one aspect of the present invention, an isolated polypeptide comprising the amino acid sequence set forth in SEQ ID NO: 8. Another aspect of the present invention includes an analog of the isolated polypeptide. Another aspect of the present invention includes a fusion protein comprising the isolated polypeptide and a heterologous polypeptide.

Some aspects of this aspect of the invention include one or more of the following. The isolated polypeptide produced by a host cell. A composition comprising the isolated polypeptide and a pharmaceutically acceptable carrier.

In accordance with another aspect of the present invention, an isolated polypeptide produced by a method including the steps of: (a) culturing a cell which comprises a nucleic acid encoding the polypeptide comprising the amino acid sequence set forth in SEQ ID NO: 8 under conditions such that the polypeptide is expressed; and (b) recovering the polypeptide.

In accordance with another aspect of the present invention, an isolated polypeptide selected from the group consisting of: (a) a polypeptide comprising the amino acid sequence set forth in SEQ ID NO:8; an (b) a polypeptide comprising amino acids 1 to 10 of SEQ ID NO:8; (c) an analog of the polypeptide comprising amino acids 1 to 10 of SEQ ID NO:8; and (d)

an analog of the polypeptide comprising amino acids 1 to 10 of SEQ ID NO:8 wherein the analog comprising a substitution of at least 1 position of the amino acids 1 to 10, the position selected from the group consisting of: 1, 2, 3, 6, 7, and n-terminal.

Some aspects of this aspect of the invention include one or more of the following. Where the isolated polypeptide consists of the amino acid sequence set forth in SEQ ID NO:8. Where the isolated polypeptide consists of amino acids 1 to 10 of SEQ ID NO:8. Where the isolated polypeptide is produced by a host cell. Where the isolated polypeptide is produced in a recombinant host cell. Where the host cell is bacterial.

In accordance with another aspect of the present invention, an isolated polypeptide as described above produced by a method including the steps of (a) expressing the polypeptide by a cell; and (b) recovering the polypeptide.

In accordance with another aspect of the present invention, an isolated polypeptide as described above produced by a method including the steps of (a) synthesizing the polypeptide of claim 7 using peptide synthesis; and (b) recovering the polypeptide.

In accordance with another aspect of the present invention, a method of sterilizing fish including administering to the fish an effective amount of a polypeptide comprising the amino acid sequence set forth in SEQ ID NO: 8 or any portion or portions of the polypeptide, an analog to said polypeptide, or an analog to any portion or portions of the polypeptide set forth in SEQ ID NO: 8.

These aspects of the invention are not meant to be exclusive and other features, aspects, and advantages of the present invention will be readily apparent to those of ordinary skill in the art when read in conjunction with the following description, appended claims and accompanying drawings.

BRIEF DESCRIPTION OF THE FIGURES

Table 1 (PRIOR ART) lists the amino acid sequences of the 15 previously known GnRH forms. The amino acid sequences of the 15 previously known GnRH forms including lamprey GnRH-III are shown along with the conventionally accepted nomenclature (GnRH peptides are usually named for the species from which they were first isolated). The different forms are grouped based on regions of similarity, with differences from mammalian mGnRH underlined (SEQ. ID. NO's 23-37);

Table 2 lists the characterized cDNA's of GnRH precursors, and their references;

Figure 2:
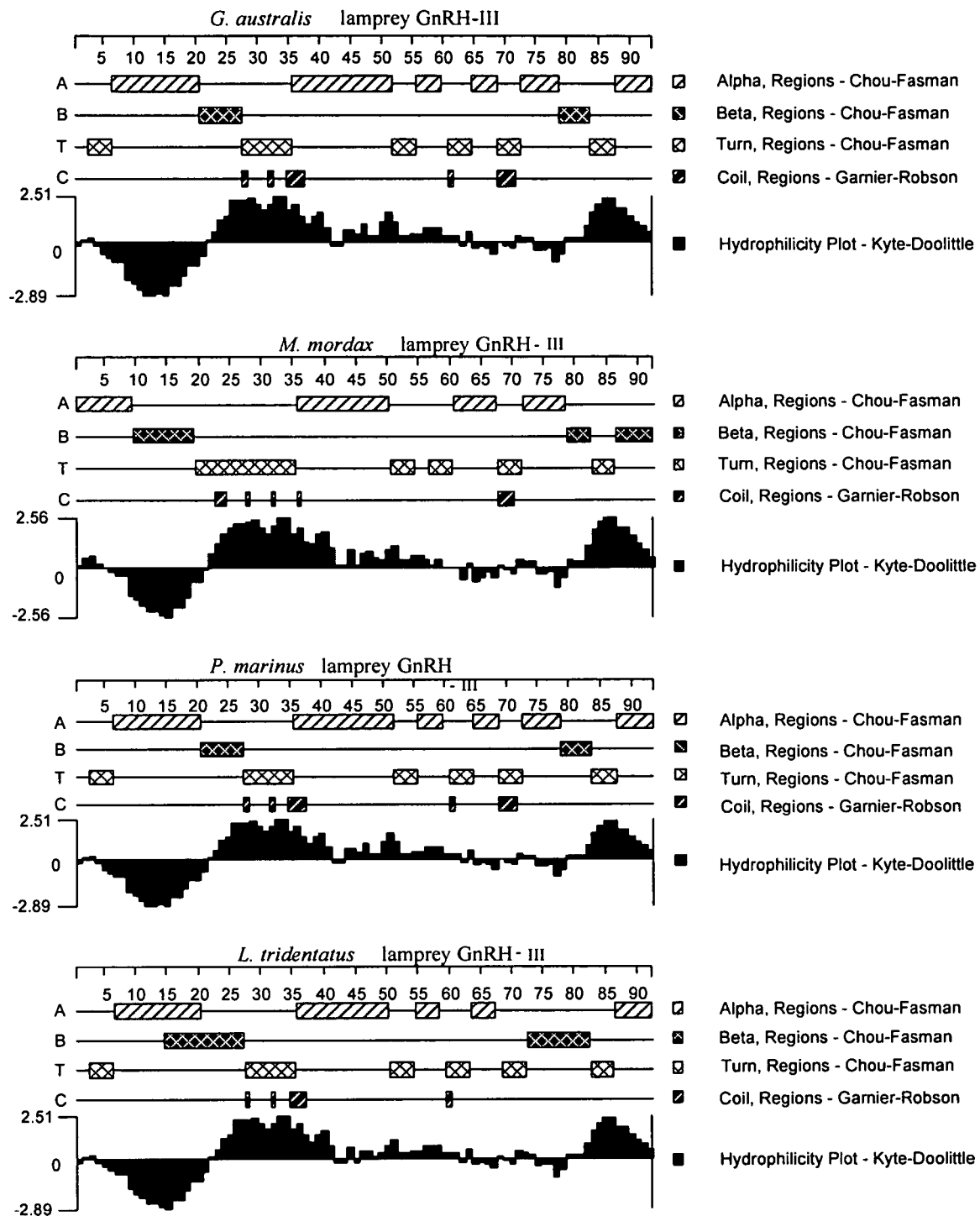
Figure 3:
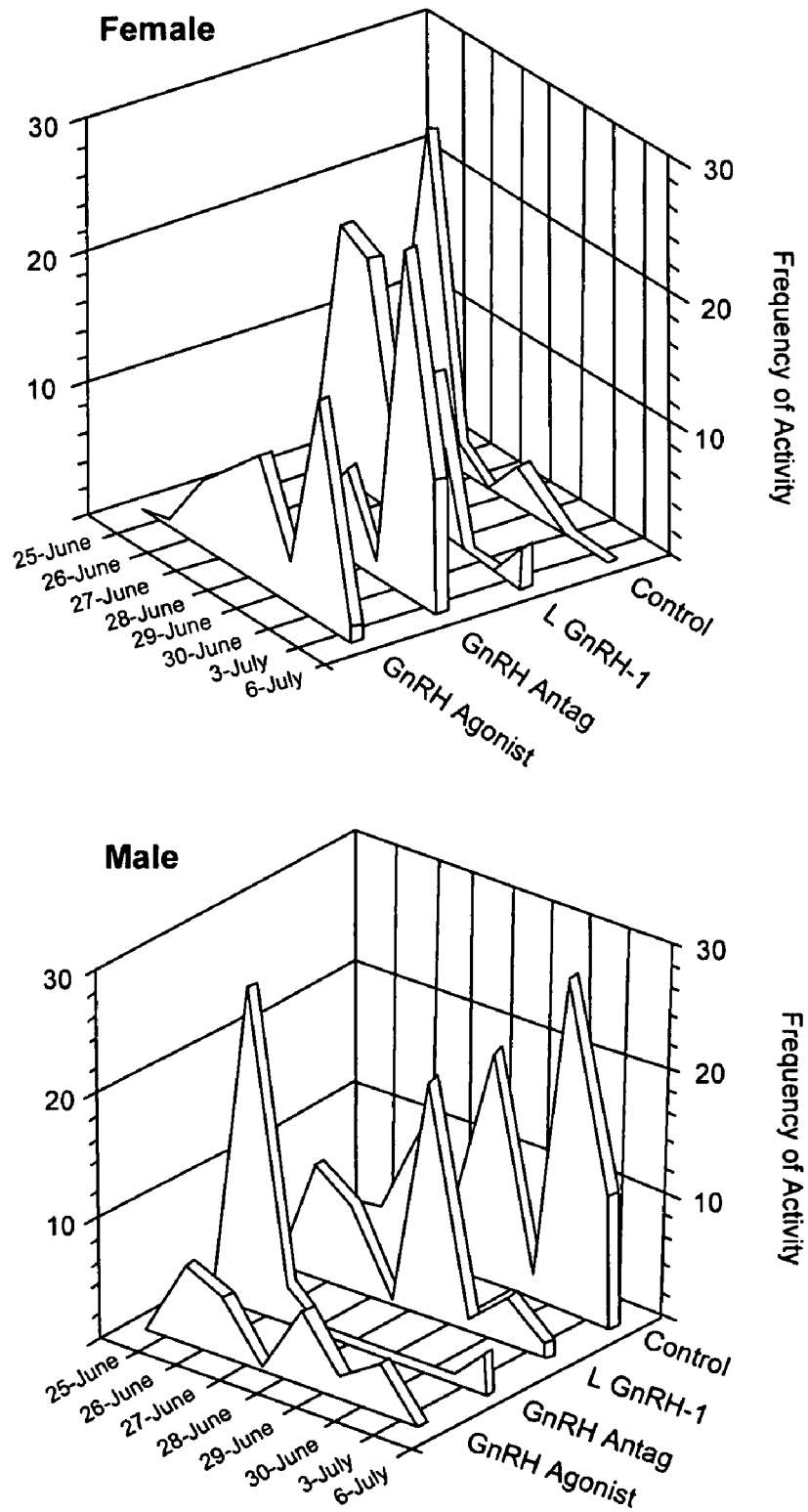
Figure 4:
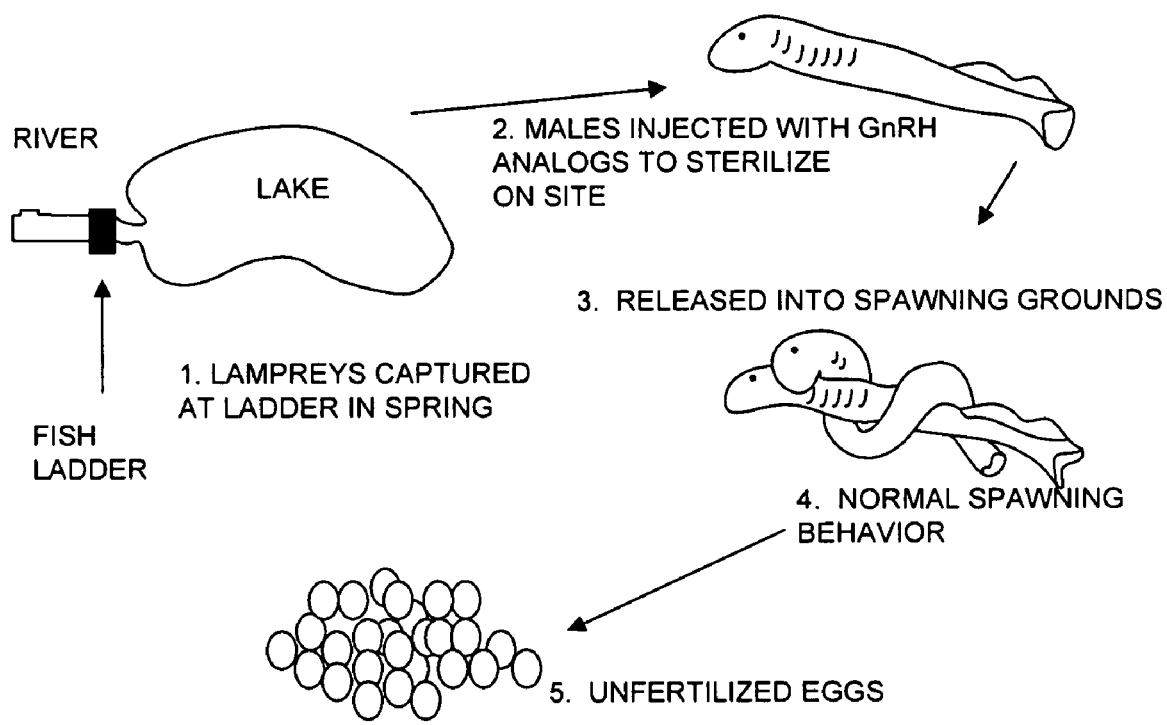

Table 3 shows the antisense primers used in 5' RACE for each respective lamprey species of the present invention (SEQ. ID. NO's 9-12);

Table 4 shows the primer pairs used in full-length transcript isolation for each respective lamprey species of the present invention (SEQ. ID. NO's 13-20);

Table 5 shows the inhibition constants ($K_I$) of lamprey GnRH-putative antagonists in the pituitary of male landlocked *P. marinus*;

FIGS. 1*a-d* list the novel cDNA's of the present invention, from 4 species of lamprey, *G. australis, M. mordax, L. tridentatus*, and *P. marinus* respectively, each encoding for the lamprey GnRH-III precursor (prepro-lGnRH-III) (SEQ. ID NO.'s: 1, 3, 5, and 7 respectively). The open reading frame of the prepro-lamprey GnRH-III from each species is underlined, while the poly-adenylation sequence is in bold. The deduced amino acid sequences of the prepro-lamprey GnRH-III peptides (hereinafter "lGnRH-III") from each respective species is below each cDNA sequence;

FIGS. 1*a-d* also show the deduced amino acid sequence of the prepro-lGnRH-III (SEQ. ID NO.'s 2, 4, 6, and 8 respectively) starting with the 24 amino acid (25 for *G. australis*) hydrophobic signal peptide which is underlined. The lGnRH-III decapeptide, is underlined and is followed by the GlyLysArg dibasic cleavage site, and the 55 amino acid GAP (GnRH Associated Peptide) region. The amino acid sequences are shown immediately below their corresponding nucleotide sequences;

FIG. 2 shows secondary structure projections for the lamprey prepro-GnRH-III's of the 4 species of lamprey, *G. australis, M mordax, P. marinus*, and *L. tridentatus* respectively;

FIG. 3 shows the results of experiments in which four groups of 12 sea lampreys each were injected two times with various compounds and behaviors of spawning activity, resting, nest building, swimming, and fanning were monitored; and FIG. 4 is a schematic illustrating a method of the invention for sterilization of male sea lamprey.

DETAILED DESCRIPTION OF THE INVENTION

The present invention includes isolated cDNA's, and the peptides encoded thereby, encoding the lamprey GnRH-III precursor, comprising the coding regions for the lamprey GnRH-III signal peptide, the lamprey GnRH-III decapeptide, the conserved cleavage site, and an associated peptide called GnRH-III associated peptide (GAP). The cDNA of the lamprey GnRH-III were isolated from 4 species of lamprey, from the three families of lamprey: *L. tridentatus*, and *P. marinus* from Petromyzonidae; *G. australis* from the Geotriidae, and *M. mordax* from the Mordaciidae.

The present invention also provides methods for the manipulation of ovulation and spawning in female and male fish using the lamprey GnRH peptide and analogs thereof, and methods for using the cDNA's encoding lamprey GnRH-III. Additionally, the present invention is method of producing the isolated GnRH-III polypeptides.

To date, two molecular forms of GnRH have been identified and sequenced in the sea lamprey: lamprey GnRH-I and lamprey GnRH-III (Sherwood et al., 1986; Sower et al., 1993). In addition, the cDNA of lamprey GnRH-I has been identified (Suzuki et al., 2000). In lampreys undergoing metamorphosis, there is an increase of brain lamprey GnRH-I and -III that coincides with the acceleration of gonadal maturation (Youson and Sower, 1991). In immunocytochemical studies, both immunoreactive (ir)-lamprey GnRH-I and -III can be found in the cell bodies of the rostral hypothalamus and pre-optic area in larval and adult sea lamprey (King et al., 1988; Nozaki et al., 2000; Tobet et al., 1995; Wright et al., 1994). Most of the ir-GnRH in the brain of larval stage lampreys has been shown to be lamprey GnRH-III. Thus lamprey GnRH-III may be the more active form during gonadal maturation. In addition, in females, it has been demonstrated that lamprey GnRH-III is present in higher concentrations than lamprey GnRH-I during the final stages of the reproductive season in lamprey (MacIntyre et al., 1997). Lamprey GnRH-I concentrations do not change significantly during the reproductive season, whereas lamprey GnRH-III undergoes significant increases during the same period. These results suggest also that lamprey GnRH-III may be the major form regulating reproductive processes in the female sea lamprey during the period of final reproductive maturation.

Such information, comparing GnRH of various species, also suggests that the structure and function of the GnRH's in vertebrates are highly conserved throughout vertebrate evolution.

Thus, in addition to the novel cDNA sequences of the present invention, the present invention also includes methods of manipulation of maturation and spawning of lamprey, using the cDNA's encoding lamprey GnRH-III, lamprey GnRH-III and analogs thereof, including methods of sterilization for male lamprey, and especially methods that sterilize but do not affect the spawning behavior of the males.

In addition, the present invention furthers the process of researching the evolution of reproductive biology. As noted above, lampreys and hagfish of the Class Agnatha are of particular importance in understanding endocrinological relationships since they are the modern descendants of the most primitive vertebrates available for study. They represent the oldest lineages of extant vertebrates—which evolved over 550 million years ago. Therefore, the study of lampreys and the characterization of brain and pituitary hormones in lampreys is particularly important for understanding the molecular evolution and functional diversity of reproductive hormones. In addition, understanding the function of GnRH in lamprey could have a substantial impact on our understanding of the release of gonadotropins in mammals and would also be of great value for clinical studies, thus potentially yielding further valuable insight into human reproductive processes.

This invention relates to a form of GnRH, particularly lamprey GnRH-III, and its novel cDNA in four species of three families of lamprey. The invention is based on the isolation and sequencing of cDNA for lamprey GnRH-III from members of the three families of lamprey in order to assess their phylogenetic relationship and provide insight into the evolution of neuroendocrine hormones, specifically the evolution of the GnRH decapeptide, and its function and regulation in lamprey and other animals.

The DNA molecules of the present invention and the endogenous GnRH peptides encoded thereby as described in FIGS. 1a-d, analogs and/or fragments thereof, and/or any combination of such endogenous and/or analog peptides and/or fragments thereof, including the signal and GAP peptides and/or analogs and/or fragments thereof (hereinafter referred to as "active compound") may be used to induce or inhibit gonadal development, and to induce and synchronize ovulation, spawning, sperm production, and spermiation. Additionally, Applicant's lamprey GnRH-I and III, and the cDNA of lamprey GnRH-I and III can be used to develop additional analogs for use in reproductive management of lampreys and therapies for other animals, including humans.

As has been shown, the lamprey l-GnRH-III has a similar amidated decapeptide structure to other GnRH's, but has unique (vs. mammalian GnRH) residues at positions 5-8. (See Table 1). Note also that while Table 1 shows the first amino acid of the l-GnRH-III peptide as pGlu, and FIGS. 1a-d show the first amino acid of the peptide as Gln, the Gln becomes pGlu in post-translational processing to result in the mature peptide. Thus, Table 1 lists the mature peptides, after processing. Note also, as shown in FIGS. 1a-d, that the 10 amino acid sequence of the decapeptide is the same for all 4 species of lamprey studied with respect to the present invention.

In addition, lampreys are among the few vertebrates to clearly demonstrate roles for multiple GnRH molecules as neurohormones involved in pituitary-gonadal function. Because lampreys have two GnRHs that act as neurohormones controlling the pituitary-gonadal axis and act in a differential manner, it is proposed that an analog to lamprey GnRH-III can be developed in which the spawning behavior would not be affected, yet the lampreys would be sterilized. Such analogs of GnRH may potentially be used to replace Bisazir in the Great Lakes lamprey sterilization program mentioned above. Thus GnRH analogs have the potential to provide a much easier, less expensive and safer method and system for controlling or regulating the lamprey reproduction. Example analogs and methods for sterilizing lamprey are described below Endogenous lGnRH-III peptide may be isolated from lamprey brains using standard techniques as described below. In the alternative, active compound may be chemically synthesized using standard automated laboratory techniques. In accordance with the invention, active compound may be formulated for use in any of a variety of methods well known in the art and active compound of the invention may be administered by any of a variety of methods known in the art. Examples of various formulations and methods will be described below.

For example, the compositions of the present invention, as would be used on lamprey or other fish or animals, are preferably administered in a "sustained release" method. The term "sustained release" is understood to mean a gradual release of active compound in a controlled manner. Such sustained release formulations of active compound may be solid and may be prepared in any suitable form such as pellets, discs or rods, or encapsulated in microspheres. Active compound may be administered by methods including implantation of a unit of active compound in the form of pellet, disc, rod, or microsphere, or injection of active compound—either intramuscular, subcutaneous, or intraperitoneal in the form of a suspension of mini-rods or microspheres. Injectable formulations in accordance with the invention in the form of mini-rods or microspheres should be sufficiently small to pass through a syringe. Injectable formulations would be suspended in an injectable solution such as saline or various buffers prior to injection. Certain methods and formulations such as microspheres for microencapsulation are covered by various U.S. patents to Zohar.

Implantable compositions usable with the present invention may preferably comprise about 300 ug of the active compound per unit. When administering an injectable composition in accordance with the invention, the administered composition will preferably comprise about 5-200 ug of the active compound per kg of body weight of the injected fish or other animal. However, the amount of the active compound may, in some cases, be reduced if a very active analog is used.

As will be discussed in more detail later, Table 5 shows various l-GnRH-III analogs used in lamprey sterilization experiments. As noted, the DNA molecules of the present invention may be used to either induce or inhibit gonadal development, and to induce and synchronize ovulation, spawning, sperm production, and spermiation. In order to induce or inhibit various sexually reproductive activities, active compound comprised of other than the mature peptide or fragments or analogs thereof, may be made using the precursor cDNA, or a portion thereof (for example, a portion encoding the signal peptide, the l-GnRH-III decapeptide and/or the GAP) and may also, or in the alternative, be administered into fish. One method of such administration may be transfection. Transfection may be achieved, for example, by microinjection, retroviral-mediated integration, electroporation, liposome-mediated delivery, and by high velocity microprojectiles. For a review of such transgenic systems in fish, see Chen et al., 1990, *Tibtech* 8:209-215 which is incorporated herein by reference in its entirety.

In addition, such a transfected coding sequence may be operatively linked to an inducible promoter using standard laboratory techniques routinely practiced in the art, such that expression may be controlled experimentally. See for example, Ausubel F. M. et al., eds., 1989 Current Protocols in Molecular Biology, Vol. I, Green Publishing Associates, Inc., and John Wiley & Sons, Inc., New York; and Sambrook et al., 1989, Molecular Cloning: A Laboratory Manual, Cold Spring Harbor Laboratories Press, Cold Spring Harbor, N.Y., which are incorporated herein by reference in their entireties. Controlled induction may result in an increase in expression at the appropriate stage of development. Such controlled induction of expression is particularly useful in the production of brute stock for fish breeding, or even use for fertility and reproductive treatments in other animals.

As noted above, the inhibition of gonadal development may be used in order to produce sterile fish and may be achieved by the negative regulation of GnRH. In addition to GnRH analogs that have the potential to provide a much easier, less expensive and safer method and system for controlling or regulating lamprey (or other species) reproduction, other compounds and methods may be useful to inhibit gonadal development. Among the compounds which may exhibit the ability to negatively regulate GnRH are: antisense, ribozyme, and triple helix molecules. Such molecules may be designed to reduce or inhibit either wild type, or if appropriate, mutant target gene activity. Techniques for the production and use of such molecules are well known to those of skill in the art.

Anti-sense RNA and DNA molecules act directly to block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, would be preferred.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. The composition of ribozyme molecules must include one or more sequences complementary to the target gene mRNA, and must include the well-known catalytic sequence responsible for mRNA cleavage. For this sequence, see U.S. Pat. No. 5,093,246, which is incorporated herein by reference in its entirety. As such, within the scope of the invention are various engineered ribozyme molecules that specifically and efficiently catalyze endonucleolytic cleavage of RNA sequences encoding target gene proteins.

The anti-sense RNA and DNA, ribozyme, and triple helix molecules of the invention may be prepared by any method known in the art for synthesis of DNA and RNA molecules. These methods include well-known techniques for chemically synthesizing oligodeoxyribonucleotides and oligoribonucleotides such as for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, anti-sense cDNA constructs that synthesize antisense RNA constitutively or inducibly, depending on the promoter used, can be introduced stably into cell lines.

In addition, various well-known modifications to DNA molecules may be introduced as a means of increasing intracellular stability and half-life. Possible modifications include but are not limited to: the addition of flanking sequences of ribo- or deoxy-nucleotides to the 5' and/or 3' ends of the molecule, or the use of phosphorothioate or 2' O-methyl rather than phosphodiesterase linkages within the oligodeoxyribonucleotide backbone. Specific ribozyme cleavage sites and further details known in the art for anti-sense, ribozyme and triple helix formation and use may be found in U.S. Pat. No. 6,210,927 to Zohar (which has been incorporated herein in its entirety).

Note also that it is possible that the antisense, ribozyme, and/or triple helix molecules described herein may so efficiently reduce or inhibit the transcription (for triple helix) and/or translation (antisense, ribozyme) of mRNA produced by normal target gene alleles that the possibility may arise wherein the concentration of normal target gene product present may be lower than is necessary for a normal phenotype. To ensure that substantially normal levels of target gene activity are maintained, therefore, nucleic acid molecules that encode and express target gene polypeptides exhibiting normal target gene activity may, for example, be introduced into cells via gene therapy methods known in the art, that do not contain sequences susceptible to whatever antisense, ribozyme, or triple helix treatments are being utilized. Alternatively, it may be preferable to co-administer normal target gene protein into the cell or tissue of interest in order to maintain the requisite level of cellular or tissue target gene activity.

Therefore, it can be seen that not all methods discussed or contemplated would be preferable for all situations. For example, sterilization of wild lamprey in the Great Lakes would preferably require the simplest methods necessary to prepare active compound, treat and release wild fish, preferably with, for example a single injection. Described below are some specific non-limiting examples and experiments.

Isolation and Sequencing of cDNA's

In the present invention, the cDNA of the GnRH-III was isolated from lamprey brain and sequenced, see FIGS. 1*a-d*. The isolated cDNA of lamprey GnRH-III codes for a GnRH signal peptide, the lGnRH-III decapeptide, the cleavage site, and an associated peptide called GnRH associated peptide (GAP). Such a cDNA may be isolated by standard laboratory techniques such as those described in detail below.

The DNA molecules of the present invention may be used to: induce or inhibit gonadal development in lamprey, and to induce and synchronize or control ovulation, spawning, sperm production, and spermiation in lamprey, as well as be used to study the evolution of GnRH, to study neuroendocrine hormones in general, to study the phylogenetic relationship between the three families of lamprey, and to shed light on possible additional forms of GnRH in other animals, including primates and especially humans, for use in reproductive therapy for humans.

With the preceding background and utility in mind therefore, the invention contemplates, in addition to the DNA sequences disclosed herein:

Any DNA sequence that encodes the same amino acid sequence as encoded by the DNA sequences shown in FIGS. 4a and b;

Any DNA sequence that hybridizes to the complement of the coding sequences disclosed herein under highly stringent conditions, e.g. washing in 0.1×SSC/0.1% SDS at 68EC (Ausubel F. M. et al., eds., 1989, Current Protocols in Molecular Biology, Vol. 1, Green Publishing Associates, Inc., and John Wiley & Sons, Inc., New York at p. 2.10.3) and still encodes a functionally equivalent gene product; and/or Any DNA sequence that hybridizes to the complement of the coding sequences disclosed herein under less stringent conditions, such as moderately stringent conditions e.g., washing in 0.2×SSC/0.1% SDS at 42EC (Ausubel et al., 1989, supra), and still encodes a functionally equivalent gene product.

The invention also encompasses:

DNA vectors that contain any portion of the coding sequences disclosed herein, (see FIGS. 1a-d), and/or their complements (i.e. antisense);

DNA expression vectors that contain any portion of the coding sequences disclosed herein (again see FIGS. 1a-d), and/or their complements (i.e. antisense) operatively associated with a regulatory element that directs the expression of the coding and/or antisense sequences; and genetically engineered host cells that contain any portion of the coding sequences disclosed herein, and/or their complements (i.e. antisense), operatively associated with a regulatory element that directs the expression of the coding and/or antisense sequences in the host cell. "Regulatory element" includes, but is not limited to: inducible and non-inducible promoters, enhancers, operators, and other elements known to those skilled in the art that drive and regulate expression. The invention also includes fragments of any of the DNA sequences discussed or disclosed herein.

Materials and Methods

Animals

Adult sea lamprey were collected during their upstream migration at the Cocheco River salmon ladder in Dover, N.H. The lamprey were brought to, and maintained in, the Anadromous Fish and Aquatic Invertebrate Research Laboratory (AFAIR Lab) at the University of New Hampshire. Brain tissue from ammocoete G. australis and M. mordax was collected by Stacia Sower, Hiroshi Kawauchi, Yoriko Kawauchi, Aki Takahashi, Masumi Nozaki, and Jean Joss in Tasmania, Australia, in February of 2001. L. tridentis tissue was received from Criag Robinson from USGS in Cook Washington on Jun. 20, 2001.

RNA Extraction

RNA was extracted from 114 mg of lamprey brain tissue using ISOGEN reagent (Nippon Gene) and a diethyl-pyrocarbonate (DEPC) treated glass homogenizer (to remove RNases). This method of RNA isolation is based on the acid guanidinium thiocyanate-phenol-chloroform extraction method (Chomzynski and Sacchi, 1987). The yield of RNA was determined via optical density at 260 nm (the wavelength specific to nucleic acid absorbance), and the purity was checked via the ratio of the optical density at 260 nm and 280 nm (the wavelength specific to protein absorbance).

cDNA Synthesis

First strand cDNA synthesis was done using the First Strand cDNA Synthesis kit by Amersham Pharmacia Biotech (Buckinhamshire, England). First strand synthesis uses 5 μg of total RNA and is catalyzed using the Moloney Murine Leukemia Virus (M-MuLV) reverse transcriptase with a Notl-$dT_{18}$ primer. The RNA was denatured via a 10-minute incubation at 65° C. before being used. Denatured RNA was then mixed with 11 μL of kit reaction mixture (M-MuLV reverse transcriptase, porcine RNAguard, Rnase/DNase-free BSA, dATP, dCTP, dGTP, and dTTP in buffer), 1 μL of 200 mM dithiothreithol (DTT), and 1 μL of 5 g/L Not1-$dT_{18}$ primer followed by incubation for 1 hour at 37° C. First strand cDNA was stored at −20° C. The single strand cDNA can be amplified vial the polymerase chain reaction (PCR), as described below, or used to make second strand cDNA via the Gubler-Hoffman technique (Gubler and Hoffman, 1983), as done using the Marathon™ cDNA Amplification Kit (Clonetech, Palo Alto, Calif., USA). Second strand cDNA was synthesized from single stranded cDNA mixed with 48.4 μL sterile water, 16 μL 5× second strand buffer (500 mM KCl, 50 mM ammonium sulfate, 25 mM $MgCl_2$, 0.75 mM β-NAD, 100 mM Tris (pH7.5), and 0.25 mM BSA), 1.6 μL 10 mM dNTPs, and 4 μL of 20× second strand Enzyme Cocktail (6 units/μL E. coli DNA polymerase I, 1.2 units/μL E. coli ligase, and 0.25 units/μL E. coli Rnase H) followed by incubation at 16° C. for 1.5 hours. The second strand cDNA was isolated via rounds of extraction using 25:24:1 phenol:chloroform:isoamyl alcohol followed by 24:1 chloroform:isoamyl alcohol, and was finally precipitated using 4M ammonium acetate and ethanol.

Partial Isolation and Sequence Isolation Using Polymerase Chain Reaction (PCR)

The 3'-end of each cDNA was first amplified via PCR using single stranded cDNA with lamprey 3-1 (GAR-CAY-TGG-TCN-CAC-GAT-TGG) (SEQ. ID NO. 21), a degenerate primer specifically designed for this invention to the lamprey-GnRH-III decapeptide, and the Not-I universal primer (AAC-TGG-AAG-AAT-TCG-C-CCG-GAG GAA) (SEQ. ID. NO. 22) under the following conditions: 10 minute taq polymerase activation period at 94° C. followed by 35 cycles of 94° C. for 1 minute, 60.3° C. for 1 minute, and 72° C. for 1.5 minutes and finally a 10 minute extension period at 72° C. The amplified PCR product was cloned in to the pGEM®-T Easy Vector System (Promega GG, Madison, Wis., USA) and sent to be sequenced at the Core Laboratories at the University of Utah. When looking at the primer sequences, these primers are written, by convention, in groups of 3 base pairs and do not encode for amino acids and thus do not necessarily contain exact multiples of 3 base pairs.

5' Rapid Amplification of cDNA Ends (5'-RACE)

5'-RACE was performed using the Marathon™ cDNA Amplification Kit (Clonetech, Palo Alto, Calif., USA). A partially double stranded DNA adapter was ligated onto both ends of the synthesized double stranded cDNA, to which a specific primer can be used in combination with a gene-specific sense or anti-sense primer, depending on which end of the cDNA is to be amplified. See Table 3 for the various primers (SEQ. ID NO's 9-12) used with various species of Lamprey. An anti-sense gene-specific primer was used with the adapter primer to amplify the 5' end of the lGnRH-III cDNA segment, and was cloned and sequenced as described above in the preceding section.

TABLE 3

Antisense primers used in 5'RACE with each respective species of lamprey.

| Species | Primer | Sequence | |
|---|---|---|---|
| G. australis | Ga-III-RC-293-313 | ggc tct cgc tgg acg ggt tcg | (SEQ. ID. NO. 9) |
| M. mordax | Mm-III-RC-154-177 | ctg cga gag gta act gag gag gtc | (SEQ. ID. NO. 10) |
| P. marinus | L-3-RC-259-280 | ggc gct ctc gag gaa ctt ctc g | (SEQ. ID. NO. 11) |
| L. tridentatus | Lt-III-RC-429-455 | cct aca cac agc cac tct ggg aca cgc | (SEQ. ID. NO. 12) |

Full-Length Transcript Isolation

A PCR protocol similar to the protocol used for partial sequence isolation was used to isolate full-length transcripts using the polymerace chain reaction (PCR). Primers designed to the 5' and 3' ends of the lamprey GnRH-III sequences from each *P. marinus*, *L. tridentatus*, *G. australis*, and *M. mordax* where used. See table 4. (SEQ. ID NO.'s 13 and 14; 15 and 16; 17 and 18; and 19 and 20 respectively).

Through overlap of sequence fragments, the entire, novel prepro-lamprey-GnRH-III cDNA sequence has been deduced from each of the four species of lamprey studied. The entire sequence refers to the signal peptide, the decapetide, the processing site and the GAP region.

Referring specifically now to FIGS. 1*a-d*, in which the cDNA sequence is shown above the corresponding amino acid sequence, the single-letter abbreviations used for the nucleotides and amino acids are the standard abbreviations

TABLE 4

Primer pairs used in full length transcript isolation for each respective species.

| Species | 5'Primer | 3'Primer |
|---|---|---|
| G. australis | Ga-III-5'end<br>(SEQ. ID. NO. 13)<br>gat tcc gct ccg agc cgc gtt gag | Ga-III-3'end<br>(SEQ. ID. NO. 14)<br>ccg aca acg aag tgt agc cca cc |
| M. mordax | Mm-III-5'end<br>(SEQ. ID. NO. 15)<br>gca gcg gtt ctc gcc gtg gtt cg | Mm-III-3'end<br>(SEQ. ID. NO. 16)<br>ggc aaa cct aca cac agc cac tct gg |
| P. marinus | Pm-lGnRH3-5'end<br>(SEQ. ID. NO. 17)<br>gac cgt ctg gaa tca tca cag aag cc | Pm-lGnRH3-3'end-RC<br>(SEQ. ID. NO. 18)<br>ggc ctt gtt gtt acg cgt ggc c |
| L. tridentatus | Lt-III-5'end<br>(SEQ. ID. NO. 19)<br>caa cag acc gtc tgg aat cat cgc agg | Lt-III-RC-429-455<br>(SEQ. ID. NO. 20)<br>cct aca cac agc cac tct ggg aca cgc |

Sequence Analysis and Phylogenetic Analysis

The *P. marinus*, *L. tridentatus*, *G. australis*, and *M. mordax* lamprey-GnRH-III cDNA sequences were analyzed using Editseq (DNA star) and were aligned with all the other known prepro-GnRH sequences using Megalign (DNA Star). Phylogenetic analysis was performed using Phylogenetic Analysis Using Parsimony (PAUP) V4.0b8 using both maximum parsimony and the neighbor joining method. Hydrophilicity (Kyte-Doolittle) and secondary structure (Garnier-Robson) where both predicted using the protein analysis program Protean (DNA Star).

CDNA Isolation Results

The initial PCR experiment with primers Lamprey3-1 and Not-I yielded a sequence fragment from the end of the lamprey-GnRH-III decapeptide to the polyadenylation sequence in each respective species of lamprey. 5'-RACE using the primers described above produced a fragment from the 5' untranslated region, through the decapetide, and signal peptide. A full-length transcript of the prepro-lamprey GnRH-III cDNA has been isolated from each of the four species studied.

for the trivial names of the nucleotides and the more common amino acids. It is shown in FIG. 1*a* that the *G. australis* lamprey GNRN-III precursor consists of 774 nucleotides or base pairs (bp) (SEQ. ID. NO. 1) in which there is an open reading frame encoding a deduced 94 amino acid sequence (SEQ. ID. NO. 2) as shown in FIG. 1*a*.

The *M. mordax* lamprey GnRH-III precursor consists of 666 base pairs encoding a 92 amino acid sequence (SEQ. ID. NO.'s 3 and 4) respectively as shown in FIG. 1*b*.

The *L. tridenatus* lamprey GnRH-III precursor consists of 733 base pairs encoding a 92 amino acid sequence (SEQ. ID. NO.'s 5 and 6) respectively, as shown in FIG. 1*c*.

Finally, the *P. marinus* lamprey GnRH-III precursor consists of 707 nucleotides (SEQ. ID NO. 7), in which there is an open reading frame encoding a deduced 92 amino acid sequence (SEQ. ID NO. 8), as shown in FIG. 1*d*.

Primers were constructed to the very 5' and 3' ends of the cDNA to isolate a full-length lamprey GnRH-III cDNA. As with all other prepro-GnRH's, the lamprey prepro-lamprey GnRH-III's consists of a tri-partite structure with a signal peptide, lamprey-GnRH-III decapeptide and dibasic cleavage site, followed by the GAP region.

Secondary structure projections of the lamprey GnRH-III precursors were created for each species using Protean (DNA Star), as shown in FIG. 2. The signal peptide in all four species, like other prepro-GnRH, has a characteristic hydrophobic α-helical structure that ranges from the $1^{st}$ to the $24^{th}$ amino acid (residues −24 to −1 of SEQ. ID NO.'s 4, 6 and 8), except in the G. australis, which has a 25 amino acid signal peptide, as seen in SEQ. ID. NO. 2). The GAP region of the four species, although divergent in sequence, consists of a predominantly hydrophilic alpha-helical composition including four turn regions, with a propensity to form a beta-sheet between the $3^{rd}$ and $4^{th}$ turn.

The Three Families of Lamprey

Using the first strand cDNA made from total RNA isolated from the hypothalamus of Lampetra tridentatus, Geotria australis, and Mordacia mordax as the template for PCR using the lamprey3-1 primer paired with the Not-I primer, partial cDNA's were isolated encoding from the lamprey-GnFH-III decapeptide to the poly-adenylation sequence from each of the aforementioned species.

The 5' end of the prepro-lamprey GnRH-III was isolated from each of the 4 species of lamprey via 5'RACE using the gene specific primers listed in Table 3. Finally, a full-length transcript was isolated using primers designed to the very 3' and 5' end of the consensus sequence constructed from the results of the degenerate PCR and 5'RACE for each species (see Table 4).

The phylogenetic analysis using the neighbor joining method with the P. marinus, L. tridentatus, G. australis, and M. mordax prepro-lamprey GnRH-III sequences with all the other known prepro-GnRH's shows the lamprey forms grouping separately from the other three clades. In addition, the two southern hemisphere sequences are divergent from the two holarctic sequences, with m. mordax and g. australis belonging to one family and l. tridentatus and p. marinus belonging to a separate family.

Use of GnRH Analogs for Sterilization in Male Sea Lamprey

As noted above, in addition to the novel cDNA sequences disclosed in the present invention, the invention also encompasses methods of using GnRH analogs to sterilize fish, preferably in this case male sea lampreys. Putative lamprey GnRH analogs have been tested to determine those that are reproductively active in the sea lamprey. Reproductive activity was evaluated by measuring the GnRH analog's ability to stimulate or inhibit plasma steroid levels in vivo. In addition, a pituitary perifusion method has been used to evaluate pituitary response to various GnRH analogs. Even though lamprey gonadotropins have yet to be isolated, pituitary responsiveness can be determined by the analog's ability to bind to GnRH pituitary receptors as has been previously demonstrated.

Native GnRH is susceptible to rapid degradation in the blood due to cleavage of the decapeptide, particularly at positions 5-6 and 9-10. Analogs having different amino acids at the relevant positions which render them less sensitive to such enzymatic degradation are thus preferred for use in the compositions according to the present invention. Several such analogs are shown in experiments described below.

The results of various prior experiments described below suggest that the third and sixth positions of lamprey GnRH-I and the sixth position of lamprey GnRH-III are important for function, because they affect the secretion of steroids from gonads. Based on these and other mammalian and teleost studies, Applicant's data suggest that other analogs with substitutions of bulky aliphatic amino acids in the second, third and sixth position of lamprey GnRH-I and -III are likely to be the best analogs for sterilization.

Additional active agents may include, for example, substitutions of positions 6 and/or 7 of the endogenous residues with hydrophobic residues such as D-Trp, for position 6, and L-Trp for position 7. Such substituting amino acids and amino acid derivatives may occur singly or in combination with one another. A list of additional potentially suitable substitute amino acids and amino acid derivatives contemplated by the invention may be found in U.S. Pat. No. 4,410,514 to Vale et al. for GnRH Agonists, which is incorporated herein by reference for suitable amino acids and derivatives.

The endogenous lGnRH peptide used in the experiments described below may be isolated from lamprey brains using techniques described above. Such peptides and analogs may also be chemically synthesized using standard automated laboratory techniques.

The effects of mammalian and lamprey GnRH analogs are summarized in the following paragraphs. In early studies, injections of a synthetic agonist of mammalian GnRH ([D-Ala$^6$, Pro$^9$]Net mammalian GnRH) significantly elevated plasma estradiol and advanced ovulation by at least several weeks in adult female lampreys (Sower et al. 1983). In this same study, a mammalian GnRH antagonist ([Ac-3 Pro$^1$, 4-FD-Phe$^3$, D-Trp$^{3,6}$] mammalian GnRH), which is a competitive inhibitor of GnRH in mammalian systems, had no apparent effect on plasma estradiol concentrations or on timing of ovulation. These data confirmed that the receptors for GnRH in the sea lamprey are specific and can distinguish between variants in this molecule. [D-Phe$^{2,6}$, Pro$^3$] lamprey GnRH was one of the first GnRH analogs tested in lamprey and found to be a putative antagonist. It inhibited ovulation in mature female lampreys, and inhibited spermiation and reduced plasma progesterone levels in the male sea lampreys (Sower, 1989; Sower et al., 1987).

Additionally, some GnRH analogs (but, to date, no analogs of lGnRH-III) have been shown to influence the spawning behavior of lampreys—actually enhancing the spawning act rather than decreasing it. Earlier studies investigated the effects of GnRH and analogs on spawning behavior in adult male and female sea lamprey during three successive spawning seasons (Sower and Hanson, 1992). In each of these experiments, three or four groups of 12 sea lampreys each were injected two times with saline, lamprey GnRH-I, lamprey GnRH agonist [D-Ala$^6$, Pro$^9$ Net lamprey GnRH] or a GnRH antagonist [D-Phe$^{2,3}$, Pro$^3$ lamprey GnRH]. After the second injection, the lampreys were introduced into an artificial stream channel and behaviors of spawning activity, resting, nest building, swimming and fanning were monitored. The lampreys were observed four times daily for 10 minutes every ½ hour during 2 hour periods (Exp.'s 1 and 2) or were observed for 6 hours on a continuous basis (Exp. 3). In experiment 2, spawning behavior was inhibited in females treated with lamprey GnRH agonist or antagonist compared to controls. FIG. 3 graphically illustrates the results of experiments 1, 2 and 3, which data previously had not been compiled and comparatively illustrated and presented.

However, in the males, lamprey GnRH agonist or antagonist stimulated earlier spawning activity compared to the controls. In experiment 3, lamprey GnRH antagonist induced earlier spawning activity in males while lamprey GnRH agonist inhibited spawning activity, and lamprey GnRH delayed spawning activity compared to the controls. See FIG. 3 also. These data suggest that lamprey GnRH-I influences spawning behavior in sea lampreys. Furthermore, the responses to GnRH and analogs were different in males compared to females, suggesting that different neuroendocrine mechanisms may be involved in males vs. females.

Further similar unpublished studies with groups of lamprey, using lGnRH-III and analogs, indicated that lamprey GnRH-III does not influence the lamprey spawning behaviors (Sower, unpublished).

As an example, the effects of lamprey GnRH analogs to lamprey GnRH-III were tested on behavior, spermiation, sperm quality, egg fertilization rate, and embryo survival. Lampreys were injected 11 times over a 35 day period. Lampreys were checked for spermiation 24 hours after injection. Lampreys were tested with 0.1 ml intraperitoneal injections of saline (control) or one of the following treatments:

1) lamprey GnRH III
2) $Phe^2$ $Gly^6$ lamprey GnRH III
3) $Phe^2$ $Pro^3$ $Asp^6$ lamprey GnRH III
4) $D-Arg^6$ lamprey GnRH III
5) N Acetyl dehydro Pro'p Fluro $D-Phe^2$ $D-Trp^{3,6}$ mammalian GnRH
6) Ac $D-pCl$ $Phe^{1,2}$ $D-Trp^3$, $D-Arg^6$, $D-Ala^{10}$ mammalian GnRH Behavior was monitored for all groups. When a male lamprey was found to be spermiating, it was removed from the tank and artificially spawned with an untreated female. Spermatocrit was assessed and recorded. For determination of fertilization rates, eggs were placed in plastic petri dishes (50 mm in diameter) and held in a constant temperature incubator at 18.3° C., the optimum temperature for development of sea lamprey embryos. Fertilization rate was assessed at 24 hours post-spawning. Embryo survival to the head stage (7-8 days post fertilization) was also assessed and recorded.

Injection with some of the GnRH-III analogs advanced the timing of spermiation but did not inhibit the behavioral response or affect the other reproductive behaviors. In summary, based on the results of these experiments, analogs to lamprey GnRH-III are preferably the best candidates for use in sterilization of lampreys.

Therefore, because lampreys have two GnRH's that act as neurohormones controlling the pituitary-gonadal axis and act in a different manner, an analog to lamprey GnRH-III can be developed in which the spawning behavior is not affected, yet the lamprey would be sterilized. This aspect, of allowing spawning behavior to remain intact, (based on Applicant's finding that lGnRH-III does not influence the lamprey spawning behaviors), yet sterilizing the fish, is unexpected and important, and is a main focus of the present invention.

In another study, the binding affinity in the pituitary of male sea lampreys was determined with lamprey GnRH-I and -III analogs in an effort to better understand the structure-activity relations of the lamprey GnRH molecule (Mateme and Sower, unpublished). Competition studies were performed using the iodinated $DAla^6$, $Pro^9Net$]-mammalian GnRH as the tracer with each of the following analogs: [$D-Phe^2$, $Gly^6$]-lGnRH-I (Peninsula Labs, Cali.); and the following lGnRH-III analogs: [$D-Phe^{2,6}$, $Pro^3$], [$D-Phe^2$, $Gly^6$], and [Ac-Delta-3Pro, $4FDPhe^2$-$D-Trp^{3,6}$] from American Peptide, Cali. All lamprey GnRH analogs tested demonstrated a high affinity binding for type-I GnRH binding site while demonstrating a significantly lower affinity for the type-II site. The level of significance was P<0.0001 See TABLE 5 for the results of these experiments. The results shown in Table 5 summarize experiments using various analogs. Self-displacement with [$DAla^6$, $Pro^9Net$]-mammalian GnRH was used as a control, and demonstrated high affinity for type-I and -II binding sites.

Table 5

Inhibition constants ($K_1$) of lamprey GnRH-putative antagonists in the pituitary of adult male land-locked *P. marinus*. Affinity at the type-I GnRH-binding site was significantly higher than affinity at type-II (p>0.0001). Self-displacement assay with [$DAla^6$, $Pro^9Net$]-mammalian GnRH was used as a control and demonstrated high affinity for both GnRH binding sites. The data were plotted on a logit-log plot and the $K_1$ determined from the $IC_{50}$ using the Prism software.

TABLE 5

| | $K_1$ (type-I) (M) | $K_1$ (type-II) (M) |
|---|---|---|
| [$DAla^6$, $Pro^9Net$]-m GnRH | $3.11 \times 10^{-12}$ | $8.9 \times 10^{-8}$ |
| [$D-Phe^2$, $Gly^6$]-lGnRH-I | $1.37 \times 10^{-9}$ | $5.65 \times 10^{-6}$ |
| [$D-Phe^2$, $Gly^6$]-lGnRH-III | $3.83 \times 10^{-12}$ | $6.55 \times 10^{-7}$ |
| [$D-Phe^{2,6}$, $Pro^3$]-lGnRH-III | $3.0 \times 10^{-11}$ | $5.22 \times 10^{-5}$ |
| [Ac-Delta-3Pro, $4FDPhe^2$-$D-Trp^{3,6}$]-lGnRH-III | $7.1 \times 10^{-9}$ | $8.94 \times 10^{-6}$ |

The studies testing these analogs showed a dose-dependent displacement by the lamprey GnRH analogs, demonstrating a high affinity binding site and a significantly lower affinity binding site, suggesting therefore, that both binding sites can discriminate between GnRH molecule variants. These inhibition data, taken together with in vivo studies done in Applicant's laboratory showing a decrease in sperm motility when compared to controls, were found to correlate with previous studies where [$Gly^6$] and [$D-Phe^{2,6}$, $Pro^3$]-lamprey GnRH-I as well as [Ac-Delta-3Pro, $4FDPhe^2$-$D-Trp^{3,6}$]-mammalian GnRH antagonists were found to decrease gametogenesis in male and female sea lampreys (Sower, 1987; Sower, 1989; Sower et al., 1983). These in vivo and in vitro studies suggest that both lamprey GnRH-I and -III molecules can be used in the design of antagonists.

In another experiment, sterilization methods usable in the Great Lakes lamprey sterilization program were investigated. Applicant's research suggests that lamprey GnRH analogs may prove to be safer, less expensive chemosterilants than those currently used. However any such methods require a method of controlled or sustained release of the active compound. Sustained release is necessary because the best means for treating wild fish would be a single injection per fish, that can be done in the field.

As noted above, some non-limiting examples of methods of using and administering the active compound (GnRH, agonist, antagonist etc.) include injection intramuscularly or intraperitoneally into the animal. In preferred embodiments, the active compound may be combined with a polymer-based carrier matrix into a sustained release delivery system. A suitable carrier having sustained release properties is chosen on the basis of its gradual release properties in a solution designed to resemble a fish's plasma, such as a ringer solution, other physiological saline solutions, fish serum, or microencapsulation. The polymer-based matrix may comprise natural or synthetic, biodegradable or non-degradable polymers or copolymers known in the art. Several such examples are described in U.S. Pat. No. 5,643,877 to Zohar which is incorporated herein by reference. For additional description of other known suitable carriers and methods for administering and delivering active compound to an animal see U.S. Pat. No. 6,210,927 which has been incorporated herein by reference. Additional methods for ultrasound-mediated administration of compounds to aquatic animals are found in U.S. Pat. No. 5,076,208 to Zohar et al. which is also incorporated herein by reference. Although various methods are known for administration and delivery of active compounds, the effect of route of administration of GnRH analogs has been specifically examined in only a few fish species, and published information is scarce.

Thus, experiments were conducted to determine the optimal injection site and delivery agent that would best ensure a slow, constant release of the active compound, in this case, D-Ala$^6$ Pro$^9$Net mammal GnRH (GnRHa) over a period of four weeks. In the plasma, GnRH is easily degraded by protolytic enzymes. Therefore a simple injection will not elevate plasma GnRH levels for the duration of time required to ensure the appropriate reproductive effect. If a GnRH analog were used to sterilize wild fish, the method would have to maintain high levels of GnRH in the plasma for the length of the spawning season, or about 6 weeks in the case of sea lamprey in the Great Lakes. It was believed that controlled release of GnRH could be attained by injection of biodegradable microspheres or implants containing a GnRH analog, and experiments were performed to determine if high enough GnRH levels could be maintained for the required duration using such a method.

In Applicant's experiments microspheres (in a dose of 75 ug GnRHa/lamprey) and 2 mm implants were injected either intramuscularly (IM) or intraperitoneally (IP). At week 1, plasma GnRHa was detected in two-thirds of the lampreys injected IP, either with microspheres (5.0+/−1.3 ng/ml) or implants (1.6+/−0.3 ng/ml). Ninety percent of the lampreys injected IM with microspheres had detectable levels of GnRHa (4.2+/−1.1 ng/ml) after one week. At week 2, ninety-two percent of the lampreys injected IM with microspheres still had detectable levels of GnRHa (3.1+/−1.2 ng/ml), while less than thirty percent of the other two treatment groups (IP with microspheres and IP with implants) had detectable levels of GnRHa.

Only the lampreys injected IM with microspheres still had detectable levels of GnRHa after 3 weeks (2.9+/−1.5 ng/ml). Based on the results of these experiments, the best method of sustained release of GnRHa was determined to be via IM injection using microspheres.

In summary, putative agonists and antagonists that may be used to manipulate, enhance, or otherwise influence reproduction in lampreys have been identified. These analogs are a valuable tool in a sterile-male release program. A schematic summary representation of a method of sterilization of male sea lamprey is shown in FIG. 4. As can be seen, the males ideally display normal spawning behavior, (enabled by use of an lGnRH-III analog that does not affect spawning behavior), but would not be able to fertilize the eggs.

CONCLUSION

In summary, the cDNA encoding the prepro-lamprey GnRH-III has been isolated from four representative species from the three families of lamprey: *Petromyzon marinus* and *Lampetra tridentatus* from the Petromyzonidae; *Geotria australis* from the Geotriidaie; and *Mordacia mordax* from the Mordaciidae. The cDNA from each species was found to have an open reading frame that encoded a peptide consistent with the conserved prepro-GnRH tripartite structure; namely the signal peptide, the lamprey GnRH-III decapeptide and dibasic cleavage site, followed by the GnRH associate peptide (GAP).

Such information is extremely useful for controlling reproduction of lamprey, preferably without disturbing their normal spawning behavior, for study of lamprey and vertebrate evolution, and for providing insight into other potential forms of GnRH for use in reproductive control and/or therapy of other animals, including humans.

Based on Applicant's experiments, it is possible that a lamprey GnRH analog may present a viable alternative and/or complement to the use of bisazir for use in the sterile male release program in the Great Lakes. The active compound tested is easily injected into lampreys in the field, and can be packaged in a sustained release delivery system that allows the GnRH to be released in the lamprey for the duration of spawning season, following only a single injection. Further testing of GnRH analogs may yield even better methods of sterilization.

The advantages of using GnRH analogs for regulation of reproduction in lamprey and other animals (either for induction or inhibition of reproduction) is high because these compounds are proteins which are easily degraded within the organism, are non-toxic, are easy to administer, are low in cost and are relatively easy to synthesize. Additionally, GnRH analogs have good potential to be approved by the FDA. GnRH analogs have already been approved for use in enhancing fish reproduction in aquaculture, and an analog of GnRH is one of the leading chemical treatments for advance prostate cancer in men and endometriosis in women.

While the above description and examples disclose some preferred embodiments of the invention, the invention is not limited in scope by the specific embodiments described. The described embodiments are intended as single illustrations of individual aspects of the invention, and functionally equivalent methods and components are within the scope of the invention. There may be variations and modifications of the invention, in addition to those shown and described herein, that, while not specifically described, do not depart from the spirit and scope of the invention as described above and in the appended claims, and which will become apparent to those skilled in the art from the foregoing description and accompanying drawings. Such modifications are intended to fall within the scope of the appended claims.

What is claimed is:

1. An isolated polypeptide comprising the amino acid sequence set forth by SEQ ID NO: 8.

2. A fusion protein comprising said isolated polypeptide of claim 1, and a heterologous polypeptide.

3. The isolated polypeptide of claim 1, produced by a host cell.

4. A composition comprising said isolated polypeptide of claim 1 and a pharmaceutically acceptable carrier.

5. The isolated polypeptide of claim 1, produced by a method comprising the steps of:

(a) culturing a cell comprising the nucleic acid of SEQ ID NO: 7 under conditions such that said polypeptide is expressed; and (b) recovering said polypeptide.

6. An isolated polypeptide produced by a method comprising the steps of:

(a) synthesizing said polypeptide of claim 1 using peptide synthesis; and (b) recovering said polypeptide.

7. A method of sterilizing fish comprising administering to said fish an effective amount of a polypeptide comprising the amino acid sequence set forth by SEQ ID NO: 8.

* * * * *